United States Patent [19]
Nelson et al.

[11] Patent Number: 6,147,503
[45] Date of Patent: Nov. 14, 2000

[54] METHOD FOR THE SIMULTANEOUS AND INDEPENDENT DETERMINATION OF MOISTURE CONTENT AND DENSITY OF PARTICULATE MATERIALS FROM RADIO-FREQUENCY PERMITTIVITY MEASUREMENTS

[75] Inventors: Stuart O. Nelson; Samir Trabelsi; Andrzej W. Kraszewski, all of Athens, Ga.

[73] Assignee: The United States of America as represented by the Secretary of Agriculture, Washington, D.C.

[21] Appl. No.: 09/074,394

[22] Filed: May 8, 1998

[51] Int. Cl.$^7$ .................................................. G01N 22/04
[52] U.S. Cl. ........................................................ 324/637
[58] Field of Search .................................. 324/637, 633, 324/634, 644, 647, 638

[56] References Cited

U.S. PATENT DOCUMENTS

| | | | |
|---|---|---|---|
| 5,039,947 | 8/1991 | Kraszewski et al. .................... | 324/634 |
| 5,218,309 | 6/1993 | Nelson et al. ........................... | 324/664 |
| 5,554,935 | 9/1996 | Kraszewski et al. .................... | 324/637 |
| 5,654,653 | 8/1997 | Bechtel et al. .......................... | 324/687 |
| 5,748,002 | 5/1998 | Scott et al. .............................. | 324/633 |

OTHER PUBLICATIONS

Ghodgaonkar et al., *IEEE Transactions on Instrumentation and Measurement*, vol. 37(3), pp. 789–793, Jun. (1989).
Kraszewski et al., *Journal of Microwave Power and Electromagnetic*, vol. 31(3), pp. 135–141 (1996). (no month).
Kress–Rogers et al., *Journal of food Engineering*, vol. 6, pp. 345–376 (1987).
S. Nelson, *Cereal Chemistry*, vol. 58(6), pp. 487–492 (1981). (no month).
Meyer et al., *IEEE Transactions on Microwave Theory and Techniques*, vol. MTT–29(7), pp. 732–739, Jul. (1981).
M. Kent, *Journal of Microwave Power*, vol. 12(4), pp. 341–345 (1977). (no month).
Nelson et al., *Journal of Agriculture Engineering Research*, vol. 21, pp. 181–192 (1976). (no month).
Menke et al., *IEEE MTT–S Digest*, vol. TH2C–7, pp. 1415–1418 (1996). (no month).
Kraszewski et al., *Journal of Microwave Power*, vol. 12(3), pp. 241–252 (1977). (no month).
Trabelsi et al., *Electronics Letters*, vol. 33(10), pp. 874–876, May 8 (1997).
Trabelsi et al., *IMTC Proceedings*, vol. 1, pp. 648–652, May 19–21 (1977).
S. Nelson, *Journal of Microwave Power*, vol. 18(2), pp. 143–152 (1983). (no month).
Kraszewski, A.W., et al., "Nondestructive Microwave Measurement of Moisture Content and Mass of Single Peanut Kernels", *Transactions of the ASAE*, vol. 36(1), pp. 127–134, Jan–Feb. 1993.
Kraszewski, A.W., et al., "Microwave Resonator Technique for Moisture Content Determination in Single Soybean Seeds", *IEEE Transactions on Instrumentation and Measurement*, vol. 38(1), pp. 79–84. Feb., 1989.
Kraszewski, A.W., et al., "Moisture Content Determination in Single Corn Kernels by Microwave Resonator Techniques", *Journal Agric. Engng. Res.*, vol. 48, pp. 77–87, 1991. (no month).
Bussey, H.E., et al., "Measurement of RF Properties of Materials A Survey", *Proceedings of the IEEE*, vol. 55(6), pp. 1046–1053, Jun., 1967.

*Primary Examiner*—Josie Ballato
*Assistant Examiner*—T. R. Sundaram
*Attorney, Agent, or Firm*—M. Howard Silverstein; John D. Fado; Gail E. Poulos

[57] ABSTRACT

A method for simultaneously and independently measuring moisture content and bulk density of particulate materials using radio-frequency measurements allowing for on-line, real-time monitoring and control. Moisture and density are determined by measurements of complex permittivities. This method is based on the use of the dielectric properties of the materials for density and water content determination.

17 Claims, 18 Drawing Sheets

METHOD FOR THE SIMULTANEOUS AND INDEPENDENT DETERMINATION OF MOISTURE CONTENT AND DENSITY OF PARTICULATE MATERIALS FROM RADIO-FREQUENCY PERMITTIVITY MEASUREMENTS

BACKGROUND OF THE INVENTION

1. Field of the Invention

The present invention is a method for the simultaneous, independent measurement of the moisture content and bulk density of any hygroscopic particulate material, such as, for example, agricultural products such as grains, from radio-frequency measurements of the dielectric properties of the bulk material.

2. Description of the Related Art

Moisture content of materials is a key parameter in many research and industrial applications, including the food and agriculture-related industries. The most widely used standard techniques for moisture content determination are oven drying techniques. These techniques are based on drying samples under specific conditions, such as temperature and time, depending on the material. Besides being energy and time consuming, in some instances the representative character of the samples might be questionable compared to the whole volume or mass of material under consideration. Moreover, most industrial processes are highly automated and require real-time, on-line measurement of the moisture content.

Electromagnetic wave-interaction-based techniques meet this requirement and provide a tool for continuous measurement. In this way, by averaging, a better estimate of the moisture content can be achieved. Among these techniques, free-space microwave techniques have the advantages of being nondestructive and contactless. Therefore, they are suitable for on-line, real-time monitoring and control. However, with particulate materials, bulk density fluctuations, as material moves on a conveyor belt or flows through a pipe, can produce significant errors in moisture content determination. It is possible to reduce these fluctuations by mechanical means by keeping the layer thickness constant or by using a vibrator to maintain an average density. However, this still produces unpredictable errors in moisture content because of the density effect. In this instance, the density has to be determined by a separate method, such as gamma-ray attenuation or weighing. A separate density measurement is always an additional cost with more technical complications in the design and implementation of the measuring system.

A better alternative is to identify empirically or define theoretically density-independent functions exclusively dependent on moisture content. From an industrial perspective, the concept of density independence is a convenient solution for a cost-effective meter that fulfills specific requirements. Therefore, the density-independent functions should be easy to manipulate for moisture content computation and tolerate instabilities produced by the measuring system and the immediate environment as well. Most of the transmission systems for moisture content determination are based on the principle of two-parameter measurement, namely the attenuation $\Delta A$ and phase shift $\Delta \phi$ and use of the ratio $$\frac{\Delta A}{\Delta \phi}$$

as a density-independent function (Kraszewski et al., J. Microwave Power, Volume 12 (3), 241–252, 1977). This ratio was identified empirically and can be used only in a transmission configuration over a limited moisture content range (Menke et al., IEEE MTT-S International Microwave Symposium Digest, Volume 3, 1415–1418, 1996).

To generalize the concept of density independence, the function has to be expressed in terms of universal entities such as the dielectric properties. The dielectric properties of materials are intrinsic properties usually expressed by the relative complex permittivity, $\epsilon = \epsilon' - j\epsilon''$, where $\epsilon'$ is the dielectric constant, which represents the ability of a material to store electric energy, and $\epsilon''$ is the loss factor, which represents the loss of electric-field energy in the material. Another parameter often used to describe the amount of loss is the loss tangent, tan $\delta$, defined as the ratio $$\frac{\varepsilon''}{\varepsilon'}.$$

The dielectric constant and loss factor, as well as the loss tangent, of moist substances are generally dependent on frequency, temperature, density, and moisture content. The influence of these variables on the relative complex permittivity has been explored and reported for many materials (Nelson et al., J. Agric. Eng. Res., Volume 21, 181–192, 1976; Kent, J. Microwave Power, Volume 12 (4), 341–345, 1977; Meyer et al., IEEE Trans. Microwave Theory Techn., Volume MTT-29 (7), 732–739, 1981; Nelson, Cereal Chemistry, Volume 58 (6), 487–492, 1981; Nelson, J. Microwave Power, Volume 18 (2), 143–153, 1983; Kress-Rogers et al., J. Food Eng., Volume 6, 345–376, 1987; Kraszewski et al., J. Microwave Power and Electromagn. Energy, Volume 31 (3), 135–141, 1996).

Present state-of-the-art microwave moisture measurement systems attempt to eliminate density fluctuation effects by secondary measurements of density with gamma radiation gauges or other techniques, or by taking the ratio of attenuation and phase-shift in microwave measurements. These techniques limit the errors in moisture content determination attributable to fluctuations in bulk density, but seldom do they eliminate the density effects entirely. Also, secondary measurements of density complicate measurement systems and increase their consequent costs.

Bussey (Proc. IEEE, Volume 55 (6), 1046–1053, June 1967) discussed the use of microwave resonant cavity techniques to measure the microwave and dielectric properties of uniformly-shaped materials by measuring the shift in the resonant frequency and the change in the Q-factor for the cavity when the sample is inserted into the cavity.

A resonant cavity has been applied for determining moisture content in uniformly shaped single seeds by simultaneous measurements of resonant frequency shift and the transmission factor (Kraszewski et al., IEEE Trans. Instrum. Meas., Volume 38 (1), 79–84, 1989; J. Agric. Eng. Res., Volume 48, 77–87, 1991; U.S. Pat. No. 5,039,947 ('947), 1991). Kraszewski et al., 1989, disclose a nondestructive process for the determination of moisture content in single soybeans using a microwave resonator. A seed is placed in a microwave resonant cavity and the resonant frequency shift and change in Q-factor are measured. This process allows the measurement of moisture content of particles of nearly uniform spherical shape. Kraszewski et al., 1991 and '947 disclose a nondestructive process for determining the moisture content of particles of irregular or variable shape where the irregular or variable-shaped product is inserted into a microwave resonant cavity in a first position and the energy dissipated in the product and the shift or change in the resonant frequency (or wavelength) due to the presence of the product is measured. The orientation of the product is then changed to a second position which is rotated by n×90 degrees with respect to the maximum field vector (n is an odd integer) and the measurements are repeated.

Kraszewski et al., (Trans. ASAE, Volume 36(1), 127–134, 1993) disclose a method for the simultaneous measurement of moisture content and mass in single peanut kernels, which are also of nearly uniform shape, using microwave resonator measurements of resonant frequency and change in cavity transmission characteristics. The cavity consisted of a section of standard WR-284 rectangular waveguide (inside dimensions: 72×34 mm) 305 mm long operating in the $H_{105}$ ($TE_{105}$) mode. It was coupled with external waveguides through two identical coupling holes 20.6 mm in diameter at each end of the cavity. A PLEXIGLAS™ tube of 15.8 mm outside diameter and 12.4 mm inside diameter was installed in the center of the cavity which supports the peanut kernel at the center of the cavity.

While various methods have been developed for measurement of properties of different materials, there remains a need in the art for a method for simultaneous, independent real-time measurements of bulk density and moisture content of hygroscopic particulate materials. The present invention provides a method which is different from prior art methods and solves some of the problems associated with the measurement of density and moisture content of bulk materials.

SUMMARY OF THE INVENTION

It is therefore, an object of the present invention to provide a method for determining moisture content and bulk density of a hygroscopic and/or particulate material using radio-frequency techniques.

Another object of the present invention is to provide a method for determining moisture content of a hygroscopic and/or particulate material independent of bulk density using radio-frequency techniques.

A further object of the present invention is to provide a method for determining moisture content, independent of bulk density, of a hygroscopic and/or particulate material wherein the dielectric constant, $\epsilon'$, and the loss factor, $\epsilon''$ are measured by radio-frequency measurement techniques, and subsequently moisture content, M, is calculated according to the equation:

$$M\% = \frac{\sqrt{\xi(a_f, \epsilon', \epsilon'') - B(T)}}{a}$$

wherein $a_f$ and a are constants, B(T) is a temperature-dependent factor; all determined empirically for each type of material; and $\zeta$ is a density-independent function determined by the equation:

$$\xi = \frac{\epsilon''}{\epsilon'(a_f \epsilon' - \epsilon'')}$$

A still further object of the present invention is to provide a method for determining bulk density of a hygroscopic and/or particulate material according to the equation:

$$\rho = \frac{1}{k}\left(\frac{a_f \epsilon' - \epsilon''}{a_f}\right)$$

wherein k is a constant determined empirically for each type of material.

Another object of the present invention is to provide a method for determining, simultaneously and independently, moisture content and bulk density of a hygroscopic and/or particulate material wherein the dielectric constant, $\epsilon'$, and the loss factor, $\epsilon''$ are measured by radio-frequency measurement techniques, and subsequently moisture content, M, is calculated according to the equation:

$$M\% = \frac{\sqrt{\xi(a_f, \epsilon', \epsilon'') - B(T)}}{a}$$

wherein $a_f$ and a are constants, B(T) is a temperature-dependent factor; all determined empirically for each type of material; and $\zeta$ is a density-independent function determined by the equation:

$$\xi = \frac{\epsilon''}{\epsilon'(a_f \epsilon' - \epsilon'')}$$

wherein $a_f$ is a constant determined empirically for each material; and bulk density, $\rho$, is calculated according to the equation $$\rho = \frac{1}{k}\left(\frac{a_f \epsilon' - \epsilon''}{a_f}\right)$$

wherein k is a constant determined empirically for each type of material.

Further objects and advantages of the invention will become apparent from the following description.

with θ independent of moisture content and temperature, and a function of frequency alone.

Figure 9:
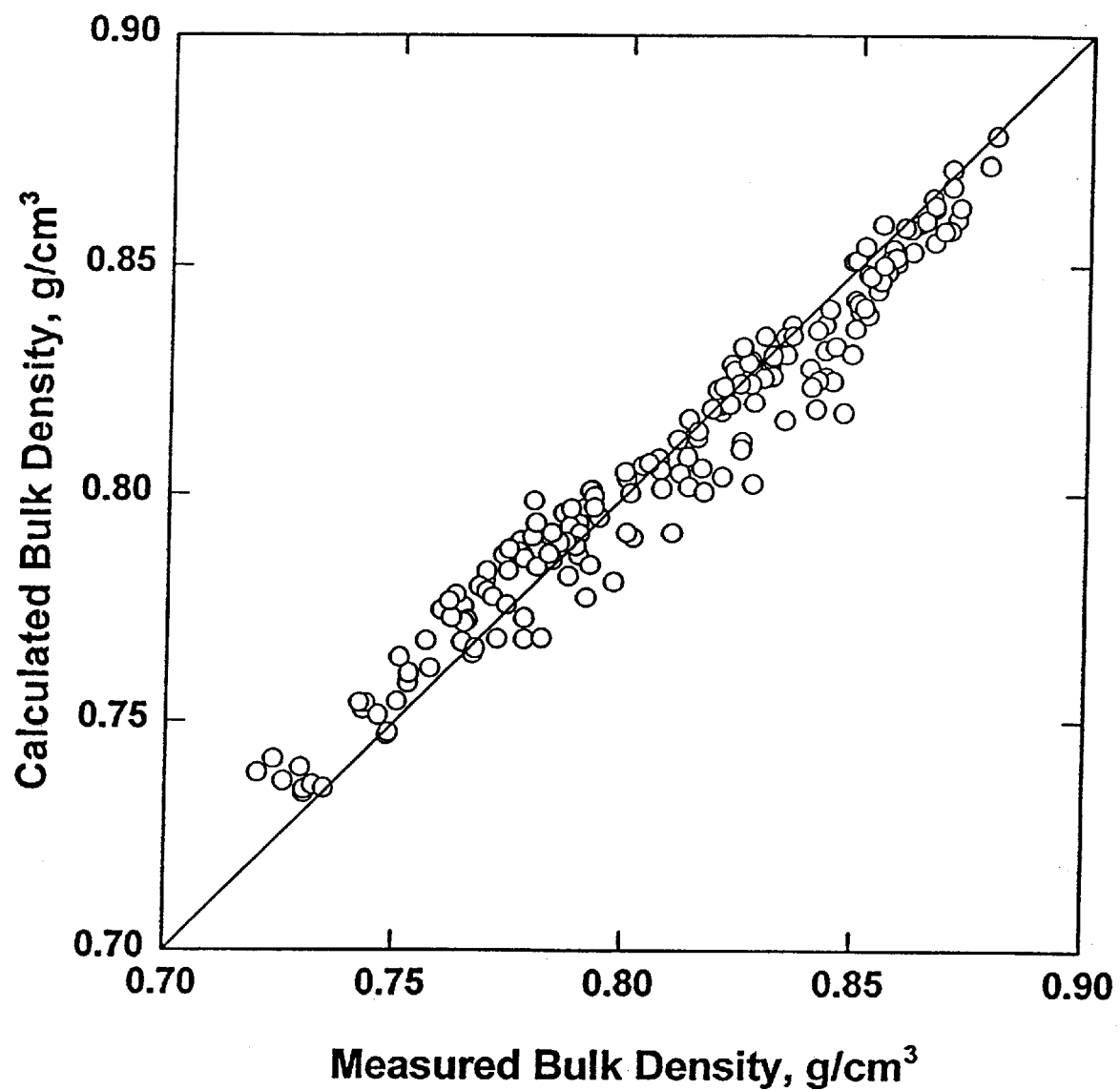

FIG. 9 is a graph showing predicted bulk density calculated by equation 6 against measured bulk density for hard red winter wheat for data obtained at 11.2 GHz.

Figure 10:
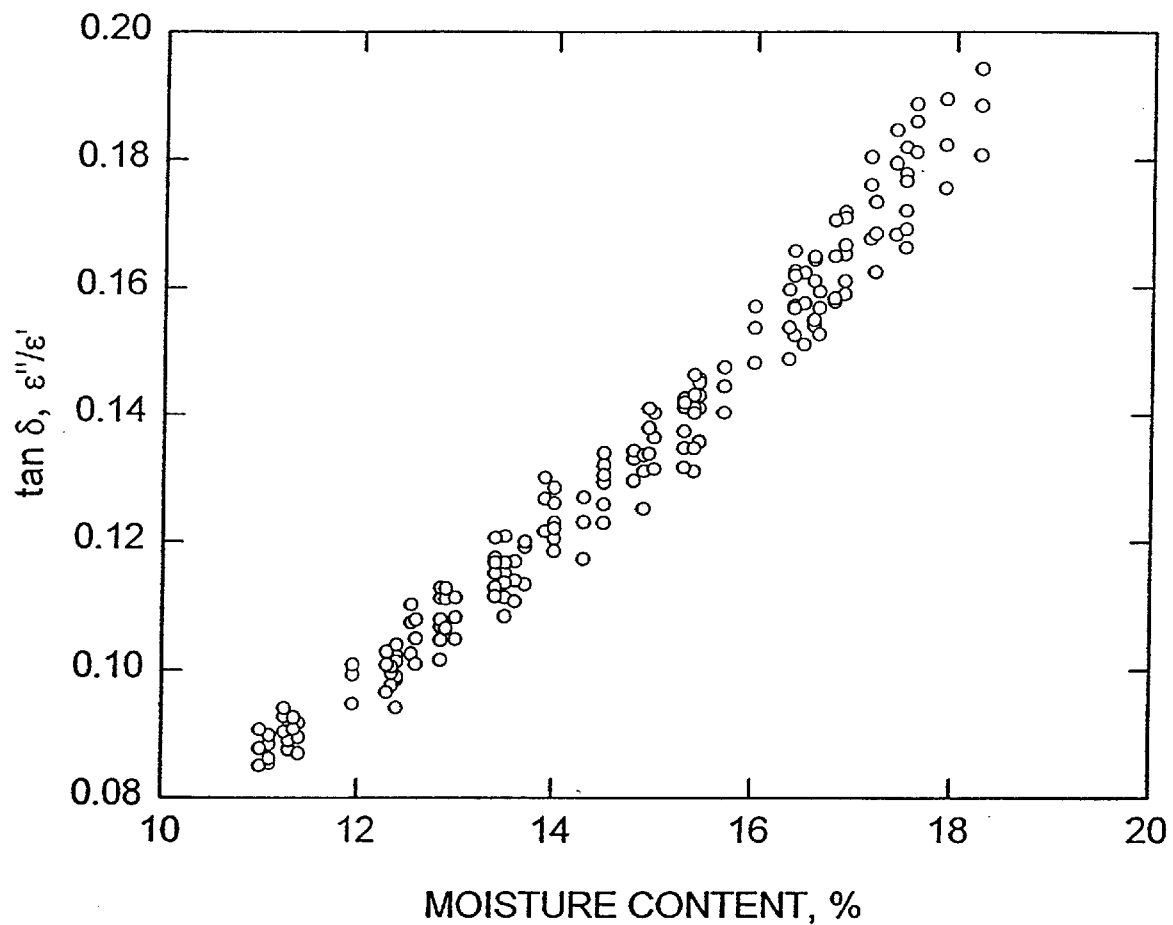

FIG. 10 is a graph showing moisture dependence of tan δ of hard red winter wheat at 14.2 GHz, 24° C., and different bulk densities ranging from loosely packed to compacted.

Figure 11:
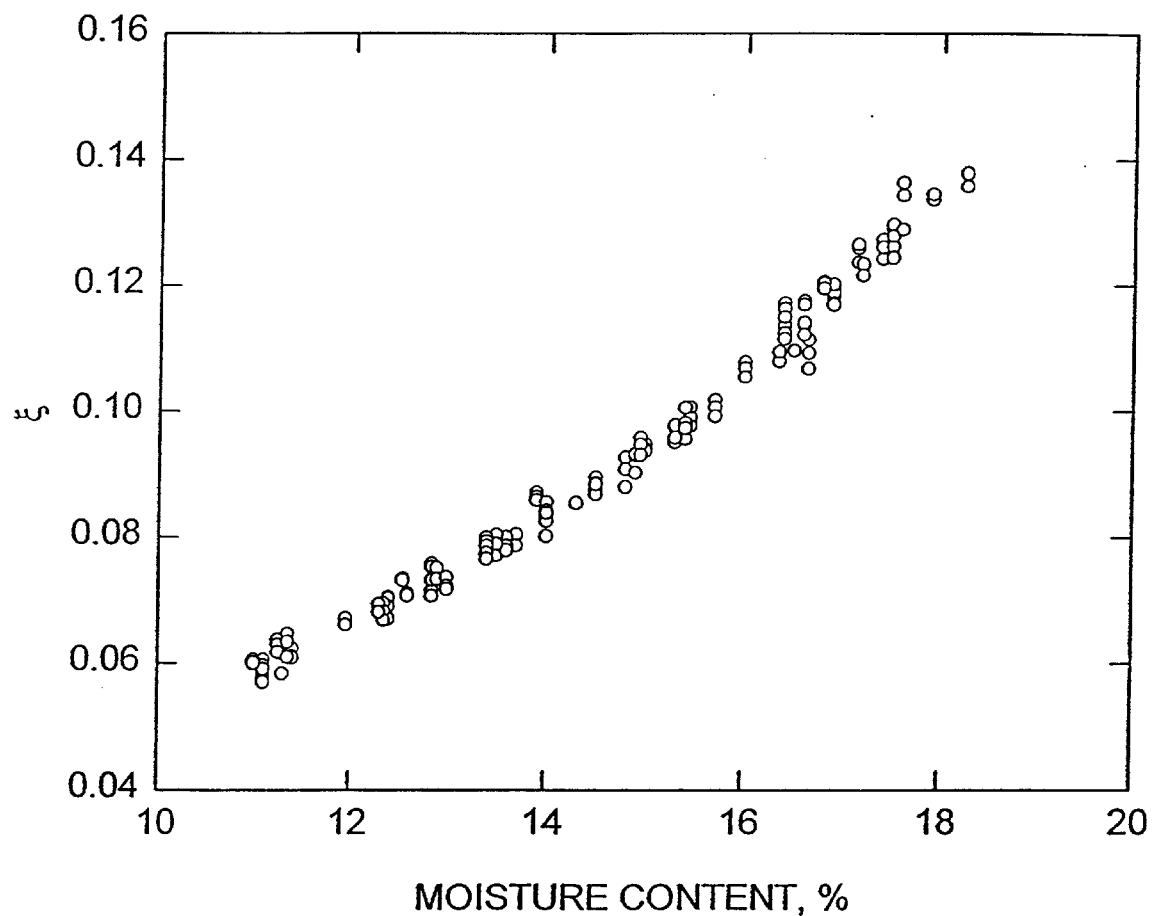

FIG. 11 is a graph showing density-independent calibration function (ζ) versus moisture content at 14.2 GHz and 24° C. for hard red winter wheat.

Figure 12:
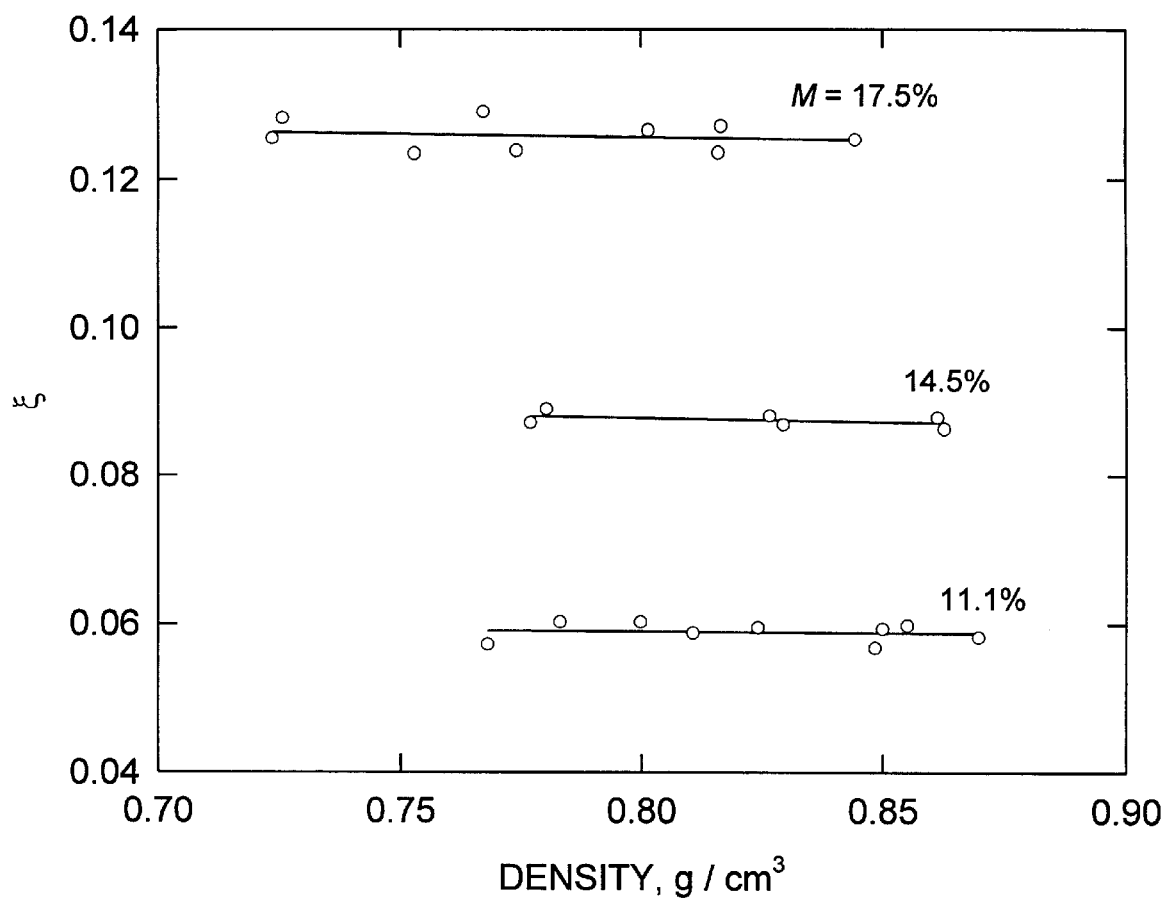

FIG. 12 is a graph showing density dependence of ζ at 14.2 GHz, 24° C., and indicated moisture contents for hard red winter wheat.

Figure 13:
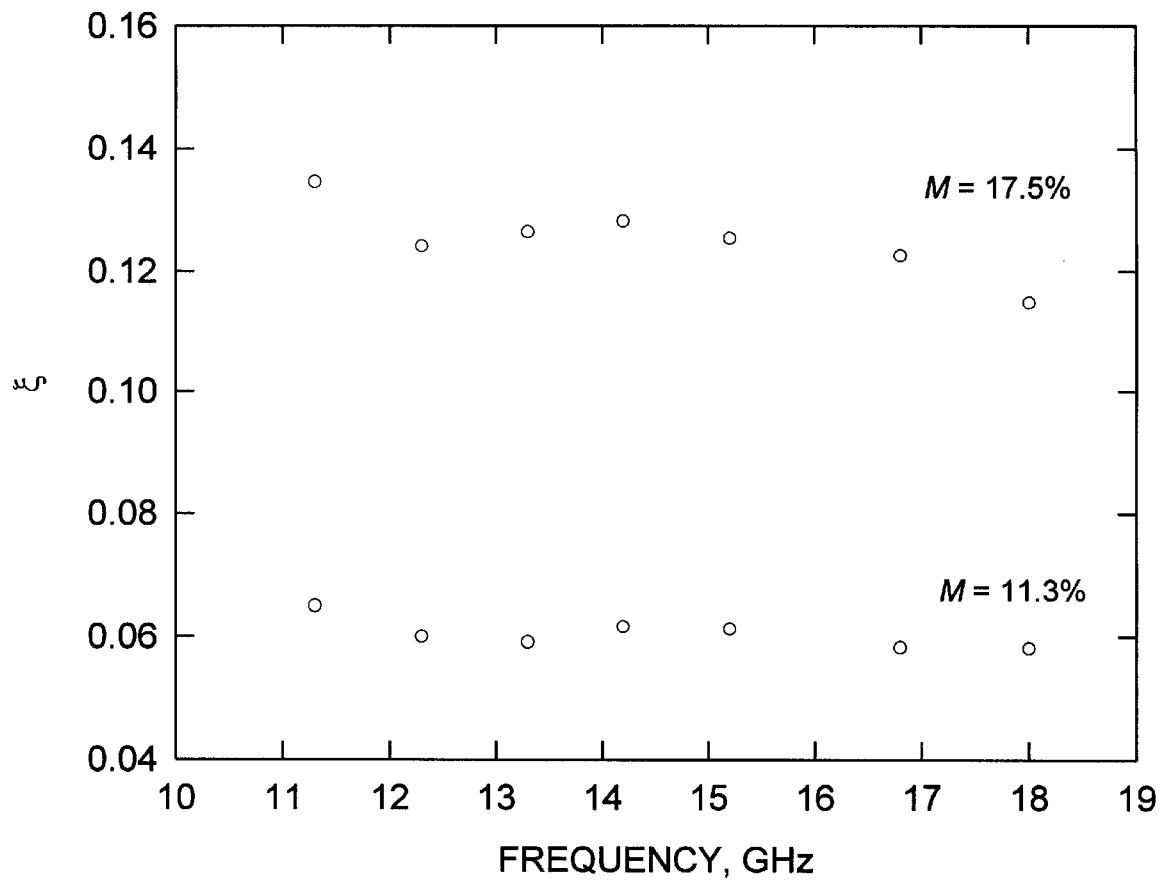

FIG. 13 is a graph showing frequency dependence of the density-independent calibration function (ζ) at 24° C. and indicated moisture contents for hard red winter wheat.

Figure 14:
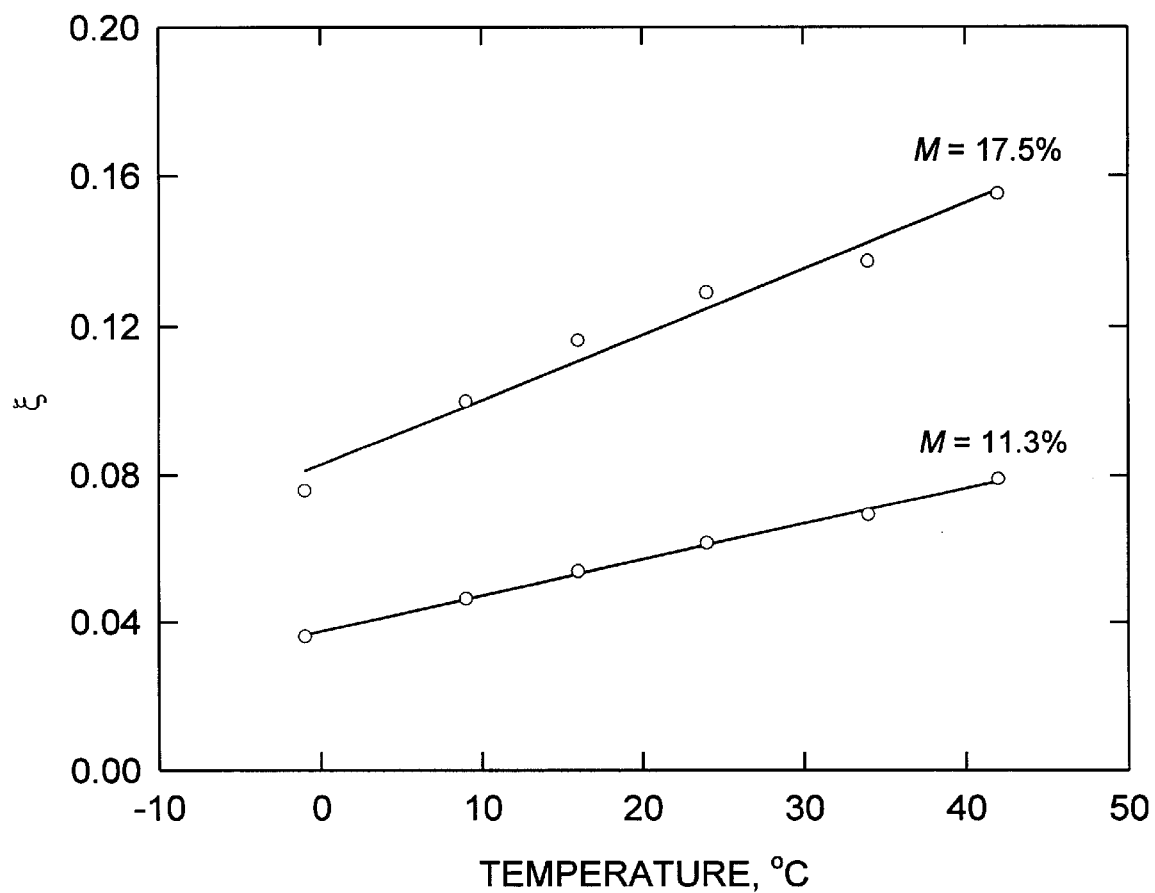

FIG. 14 is a graph showing temperature dependence of ; at 14.2 GHz and indicated moisture contents for hard red winter wheat.

Figure 15:
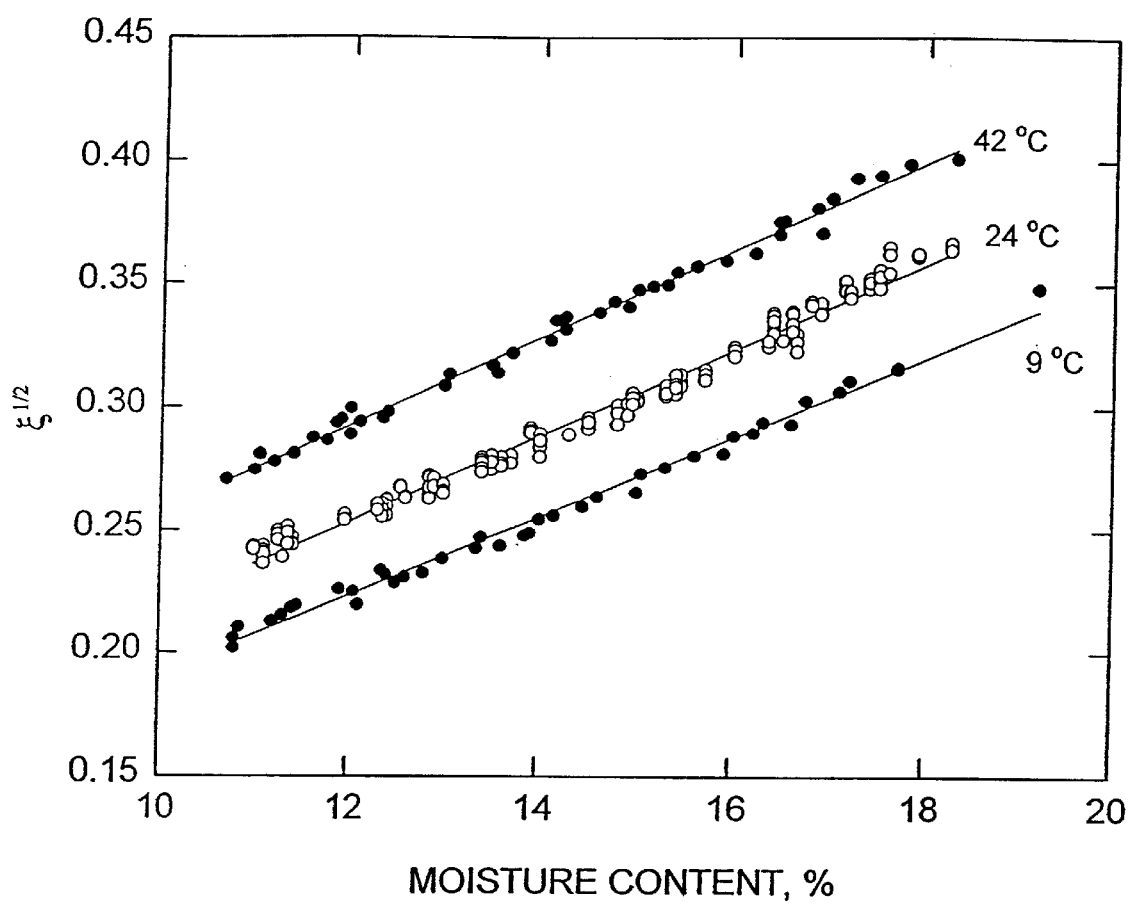

FIG. 15 is a graph showing moisture dependence of the square root of ζ at 14.2 GHz and indicated temperatures for hard red winter wheat.

Figure 16:
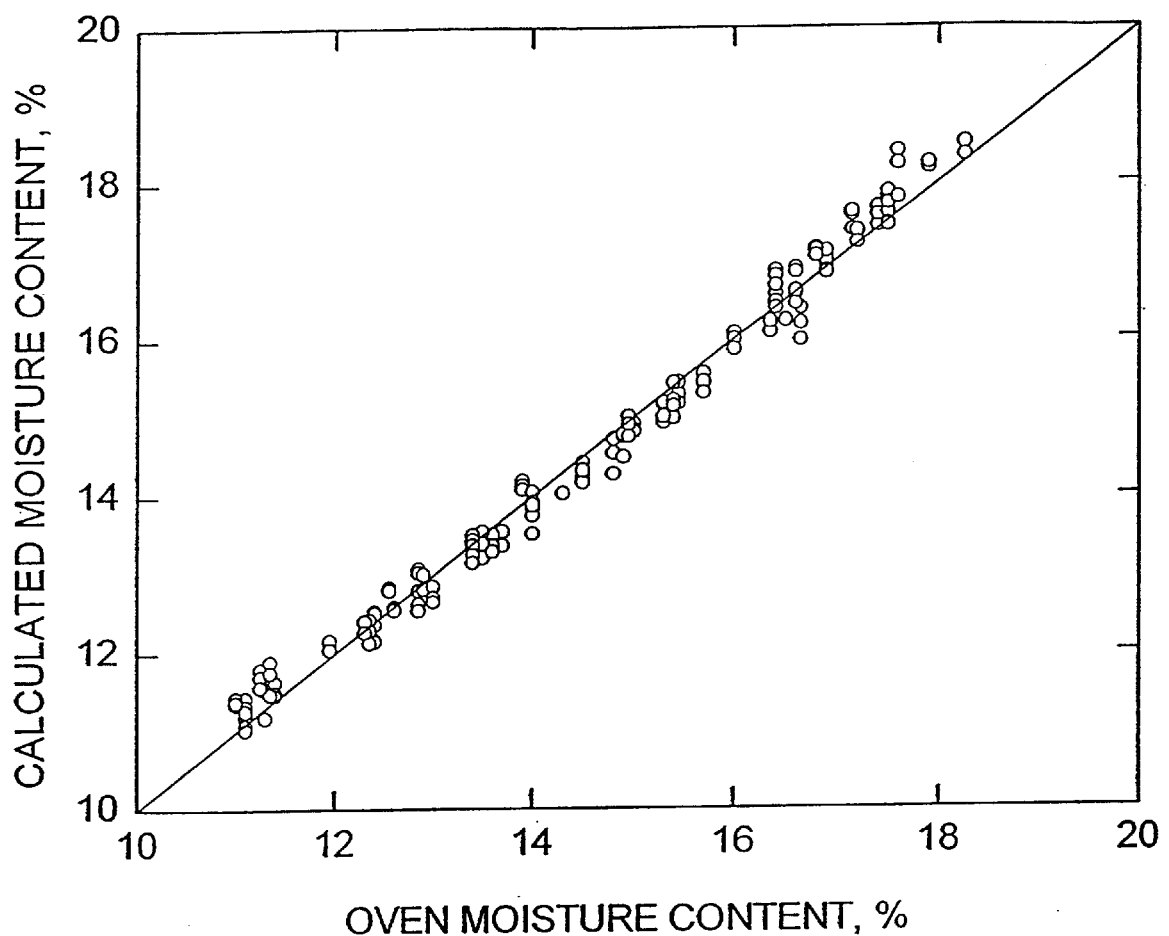

FIG. 16 is a graph showing predicted moisture content calculated by equation 14 versus oven-drying moisture content for hard red winter wheat.

DETAILED DESCRIPTION OF THE INVENTION

Radio-frequency techniques have been considered for a long time for moisture sensing in many food processing and agriculture-related industries. These techniques are suitable for on-line, real-time monitoring and control. However, with any hygroscopic and/or particulate materials, such as grains, seeds, cereal products, feeds, ground materials, pharmaceuticals, pulps such as sugarbeet pulp, soybeans, wood chips, confectionery powders, sand etc.; bulk density fluctuations cause significant errors in moisture content determination. The present invention is a new method for determining moisture content, independent of bulk density, and bulk density if needed, simultaneously using any radio-frequency measurement technique. For purposes of the present invention, the radio-frequency range is defined as being from about 10 KHz to about 300 GHz, with microwave frequencies defined as from about 300 MHz to about 300 GHz. Moisture and/or density are determined by measurement of complex permittivities at the selected frequency, such as for example, measurement of attenuation and phase-shift at microwave frequencies. An explicit relationship between the bulk density and the two components of the relative complex permittivity is identified, and a new density-independent function for moisture content prediction is defined. The universal character of this method resides in its independence of the measurement technique. Therefore, the choice of the appropriate measurement technique is mainly based on the requirements for the particular application. This universal method is needed with the growing demand for on-line, real-time determination of parameters such as density and water content. For example, an important application for this method is in control of grain drying equipment. More than seven billion bushels of corn are generally produced annually in the United States and the major portion of this production is dried before going into storage. The availability of accurate on-line moisture content sensing to control grain drying equipment could prevent overdrying or underdrying. Failure to reduce moisture level to the required point for safe storage results in losses due to fungal and insect damage. Overdrying results in loss of value because of unnecessary loss in weight of the grain and because overdried grain is subject to cracking and damage in handling equipment. Loss in value of even one tenth of one percent in half the annual corn crop would translate into economic losses of more than 10 million dollars. This is only one grain crop and only one application. Savings in milling and processing of grain and improved yields and improved grain product quality in addition to reductions in storage losses are other benefits of better management that would result from better moisture information.

Figure 1:
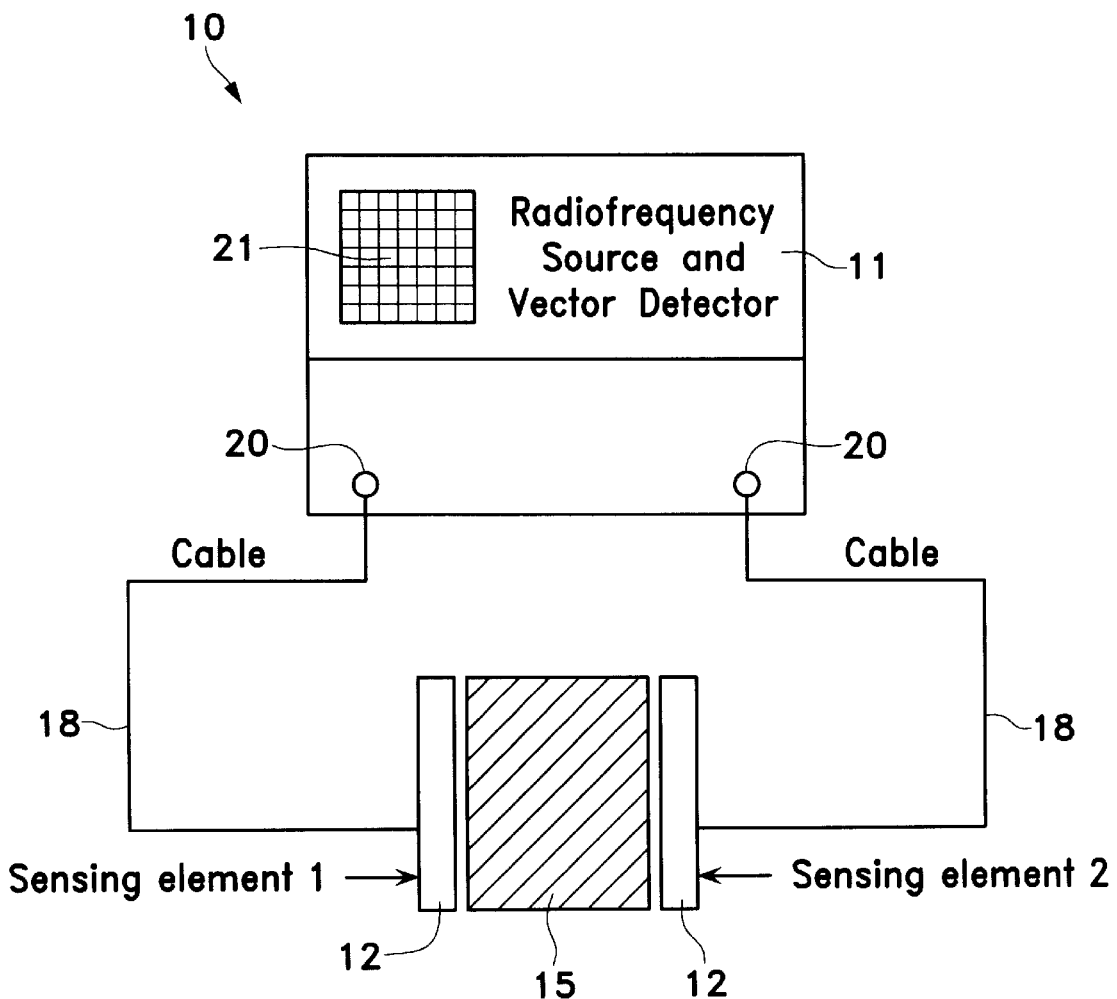
FIG. 1 is a radio-frequency measurement system diagram.
Figure 2:
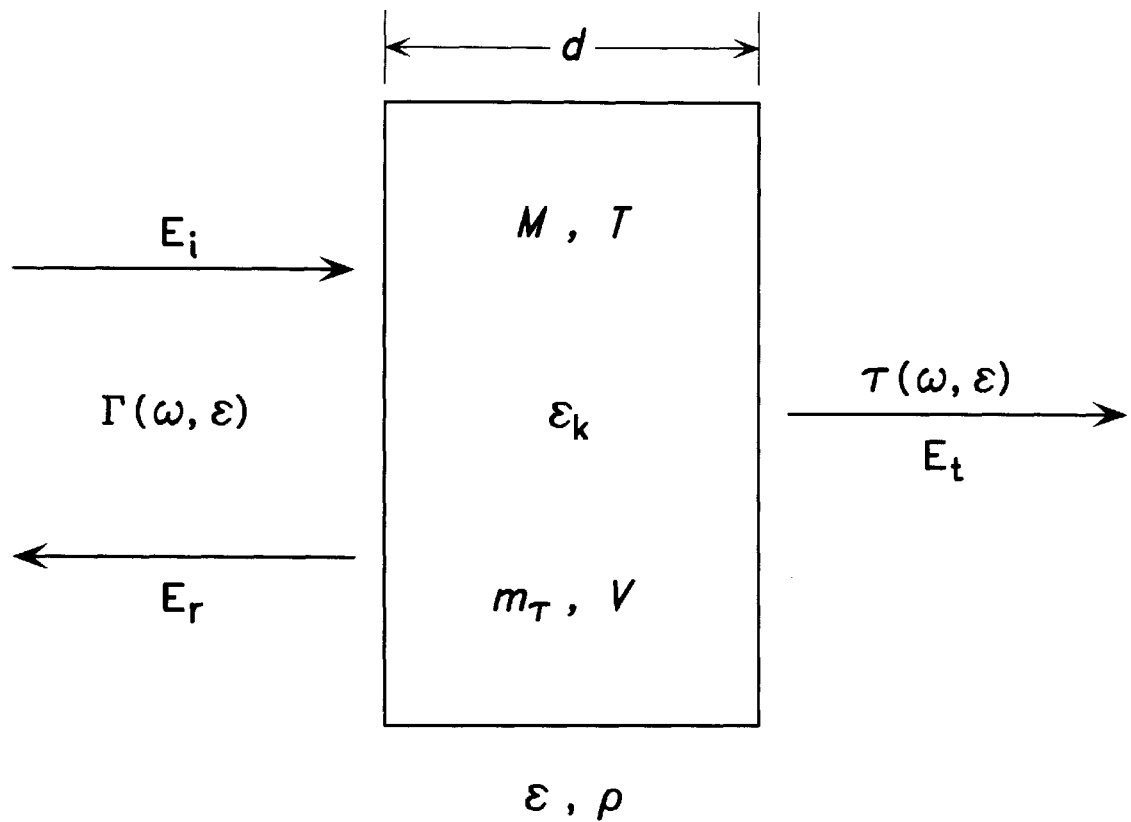
FIG. 2 is a Reflection/Transmission measurement diagram.

The permittivity is measured by any radio-frequency technique, which, according to common practice, provides reliable values for the dielectric constant and the dielectric loss factor at the frequency of interest (FIG. 1). The system 10 includes a radio-frequency voltage source 11 for providing energy for excitation of sensing elements 12, which can be, for example, electrodes, antennas, resonant structure, etc. The material 15 for measurement is usually placed, or passed between or through or in close proximity to the sensing elements 12, and a signal, which depends on the radio-frequency properties of material 15, is detected by measuring unit 21 which has the capability for a vector measurement, such as for example complex impedence, complex reflection coefficient, complex transmission coefficient, resonant frequency and quality factor, etc. For the purposes of describing the different parameters involved such as for a microwave measuring system, for example, only the reflection/transmission configuration is considered (FIG. 2) (Trabelsi et al., IMTC Proceedings, Volume 1, 648–652, May 1997; Electronic Letters, Volume 33 (10), 874–876, May 8, 1997; both herein incorporated by reference). Consider a container of thickness d and volume V filled with a nonmagnetic ($\mu$=1) hygroscopic and/or particulate material of moisture content M and temperature T. The moisture content in percent is defined as $$M(\%) = \frac{m_w}{m_t} \times 100,$$

and the bulk density p is defined as $$\rho = \frac{m_t}{V}$$

where $m_w$ and $m_t$ are the mass of water and total mass, respectively. Some of these properties are intensive and some are extensive. For example, for a homogeneous material in a container of fixed volume, M and T are intensive and are supposed to be the same throughout the entire volume, while ρ is extensive; with compaction of the material, the bulk density changes. A similar classification can be applied to the electrical parameters. The two entities accessible by measurements in a reflection/transmission configuration, are the reflection coefficient $$\Gamma(\omega, \varepsilon) = \frac{E_r}{E_i}$$

and the transmission coefficient $$\tau(\omega, \varepsilon) = \frac{E_t}{E_i},$$

where $\omega = 2\pi f$, $f$ is the frequency of the applied electric field $E_i$, and $E_r$ and $E_t$ are the reflected and transmitted electric fields, respectively. The relative complex permittivity $\epsilon$ is in fact the effective permittivity of the air-material mixture and is often calculated from $\Gamma$ and/or $\tau$ (Ghodgaonkar et al., IEEE Trans. Instr. Meas., Volume 37 (3), 789–793, 1989; herein incorporated by reference). On the material level, the permittivity of the particle $\epsilon_p = \epsilon'_p - j\epsilon''_p$, can be calculated either by applying mixture equations or by means of a model for which the electromagnetic field inside the mixture has to be defined. This is rather difficult because of the complexity of the wave-material interaction. Both permittivities can be considered as intrinsic properties of the material under test. However, at a given frequency $f$, the effective permittivity $\epsilon$ is a function of ρ, M, and T:

$$\epsilon = \epsilon(\rho, M, T) = \epsilon'(\rho, M, T) - j\epsilon''(\rho, M, T) \quad (1)$$

and thus is extensive because of its dependence on ρ, while $\epsilon_p$ is intensive and depends only on M and T:

$$\epsilon_p = \epsilon_p(M, T) = \epsilon'_p(M, T) - j\epsilon''_p(M, T) \quad (2)$$

Figure 3:
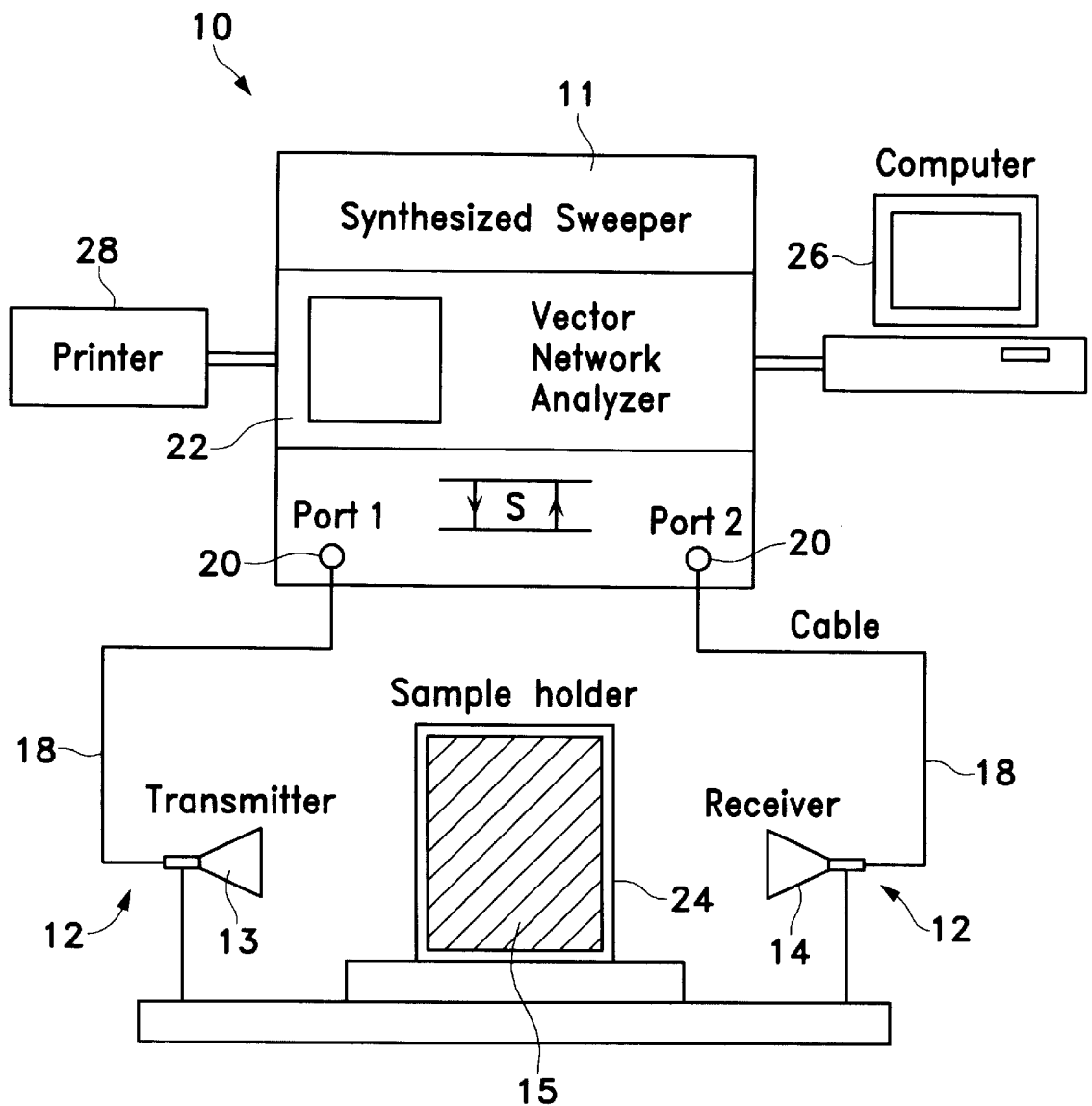
FIG. 3 is a block diagram of a microwave free-space transmission measurement set-up.

Therefore, when this relation is known, the relation between the permittivity $\epsilon_p$ and the two intensive properties M and T, is unique. At a given temperature, an explicit analytical relation between $\epsilon_p$ and M can be found. However, for the reasons mentioned supra, $\epsilon_p$ is rather difficult to obtain and thus $\epsilon$ for the air-material mixture is usually considered. In many applications, where M is the target parameter, the density fluctuation problem has to be solved. One possibility is to define a density-independent function preferably based on the effective relative complex permittivity. By way of example, when using a free-space transmission technique (Kraszewski et al., Journal of Microwave Power and Electromagnetic Energy, Volume 31(3), 135–141, 1996; herein incorporated by reference) the measuring system 10 includes sensing elements 12 which include a transmitting antenna 13 and a receiving antenna 14, which can be two matching antennas of any type (FIG. 3). Antennas 13 and 14 are each connected by coaxial cables 18 to the two ports 20 of the vector network analyzer 22 or any transmission coefficient measuring unit. The sample holder 24 is made of very low-loss material, such as for example, STYROFOAM®, which is placed between antennas 13 and 14. The sample holder shape should be selected appropriately so that the bulk density can be considered uniform throughout the sample. The sample thickness is selected so that all inhomogeneities inside the sample are well averaged and to ensure a minimum of 10 dB attenuation to minimize the effects of internal multiple reflections on transmission coefficient measurements. Errors in transmission coefficient measurement result in errors in the relative complex permittivity determination and consequently in moisture content and bulk density prediction. Particular frequencies can be selected for the best impedance matching of the antennas. These frequencies correspond to the lower SWR, typically less than about 1.2.

Once the frequencies are selected, the sample material is loaded into the sample holder 24, and the transmission coefficient is measured at the selected microwave frequencies. These measurements are converted to percent moisture, independent of the bulk density, and bulk density by computer 26 based on the following:

When a transmission technique is used, the real and imaginary parts of the relative complex permittivity are calculated from a plane wave, of normal incidence, traveling through a low-loss sample ($\epsilon'' << \epsilon'$) by the following relations:

$$\varepsilon' \simeq \left(1 + \frac{\Delta\Phi\lambda_0}{360d}\right)^2 \quad (3)$$

$$\varepsilon'' \simeq \frac{\Delta A \lambda_0 \sqrt{\varepsilon'}}{8.68\pi d} \quad (4)$$

where $\lambda_0$ is the free-space wavelength and d is sample thickness, $\Delta A$ is the attenuation measurement, and $\Delta\phi$ is the phase shift measurement measured in degrees. Both $\epsilon'$ and $\epsilon''$ are functions of the frequency $f$, temperature T, bulk density ρ, and wet-basis moisture content M. Using the complex plane representation, $\epsilon'$ and $\epsilon''$ divided by the bulk density of the sample ρ, are plotted against each other. Regardless of sample temperature or moisture content, the points $$\left(\frac{\varepsilon'}{\rho}, \frac{\varepsilon''}{\rho}\right)$$

fall on or along the straight line. The slope of the line is a function of frequency. The equation of the line can be written as $$\frac{\varepsilon''}{\rho} = a_f \left(\frac{\varepsilon'}{\rho} - k\right) \quad (5)$$

where $a_f$ is the slope of the line and k is the value $$\frac{\varepsilon'}{\rho}$$

at the $$\frac{\varepsilon''}{\rho} = 0$$

intercept. The values $a_f$ and k can be determined for a given material and then equation 5 can be solved for ρ, $$\rho = \frac{1}{k}\left(\frac{a_f \varepsilon' - \varepsilon''}{a_f}\right) \quad (6)$$

where k is in $g^{-1} \cdot cm^3$ and $a_f$, $\epsilon'$ and $\epsilon''$ are dimensionless.

For moisture content determination, a density-independent function is developed as follows:

Taking the ratio of $$\tan\delta = \frac{\varepsilon''}{\varepsilon'}$$

to bulk density, ρ, provides a density-independent function ψ, which, for a given frequency and material, can be expressed as $$\psi = \frac{ka_f}{a_f\varepsilon' - \varepsilon''}\left(\frac{\varepsilon''}{\varepsilon'}\right) \quad (7)$$

At a given frequency and for a given material, the product $ka_f$ is a constant; thus equation 7 can be simplified, giving a density independent function $$\xi = \frac{1}{a_f\varepsilon' - \varepsilon''}\left(\frac{\varepsilon''}{\varepsilon'}\right) \quad (8)$$

Since ζ is a quadratic function of moisture content, M (See FIG. 11), √ζ is considered, and M can be expressed as a function of the permittivity components, ε' and ε" and constants determined empirically for any given material. Thereby, both moisture content and bulk density of the sample are determined when the permittivity, values of ε' and ε" are known. Since these are intrinsic properties of the material, their values may be sensed by any practical measurement technique providing a method for determining moisture content, independent of bulk density, and also the value of bulk density, if needed, at the same time.

The following example is presented to illustrate the use of the present invention for density-independent determination of moisture content of hard red winter wheat and the density of these materials when needed using microwave transmission measurements as a test model system. These examples are intended to further illustrate the invention and are not intended to limit the scope as defined by the claims.

EXAMPLE 1

Measurements on hard red winter wheat, over wide ranges of frequency, temperature, moisture content and bulk density are taken using a free-space transmission microwave technique (Kraszewski et al., 1996, supra). The wheat kernels were poured into the sample holder 24, which has a rectangular cross section, so that they formed a homogeneous layer of constant thickness, d=10.4 cm. As the wave propagates through the layer of material, it is attenuated and the phase shifted. The attenuation and phase shift are measured by means of a vector network analyzer (Hewlett-Packard 8510B) calibrated in the transmission mode. The measurements were performed at selected frequencies for two cultivars of hard red winter wheat, *Triticum aestivum* L., 'Karl' and 'Arapahoe', grown in Nebraska (USA) in 1992 and 1994, respectively. These frequencies correspond to the best matching of the two antennas with the empty sample holder between them.

Sublots of different moisture contents were prepared by spraying distilled water on the wheat kernels and storing them in sealed jars for about 72 hours at about 4° C. to equilibrate. Each sample was mixed periodically by rotating the sealed jar so that the moisture content was uniform throughout the entire sample.

Before microwave measurements were performed, the sealed samples were allowed to equilibrate to room temperature (approximately 24° C.±1° C.) for at least about 24 hours. The moisture content of each sample was determined by a standard oven method (ASAE, 1995, ASAE Standards 1995: ASAE S352.2, Moisture Measurement-unground grain and seeds. ASAE, St. Joseph, Mich.;

herein incorporated by reference) immediately after the microwave measurements. This standard specifies drying unground 10-gram samples of wheat for about 19 hours at about 130° C. Seventy-one moisture levels were measured for the two wheat cultivars.

For each sample, the bulk density was gradually increased by settling the grain in the sample holder and adding more kernels. The microwave measurements were repeated for at least three different bulk densities ranging from loosely packed to compacted.

Measurements were also taken at temperatures below and above room temperature, approximately 24° C. Sealed samples of various moisture contents were allowed to stabilize for three days in a chamber where the temperature was adjusted to the desired level. For some samples, temperature was checked before and after the microwave measurement. On average, temperature was stable within about ±0.5° C. An extensive data set was obtained over wide ranges of frequency, approximately 11 to 18 GHz; moisture content, about 10.6% to about 19.2%, wet basis; bulk density, loosely packed to compacted by settling of the sample; and temperature, about −1° C. to about +420C.

Figure 4A:
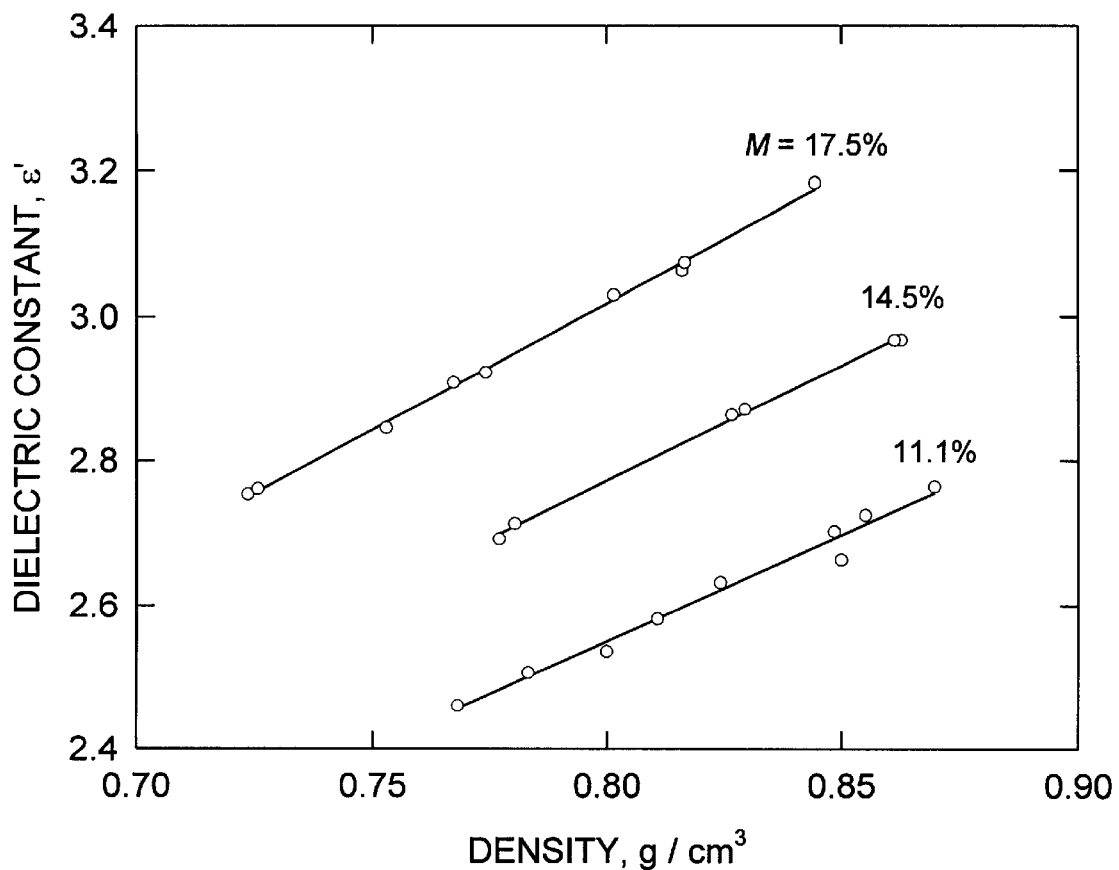
FIG. 4a is a graph showing the density dependence of the dielectric constant of hard red winter wheat at 14.2 GHz, 24° C. and indicated moisture contents.
Figure 4B:
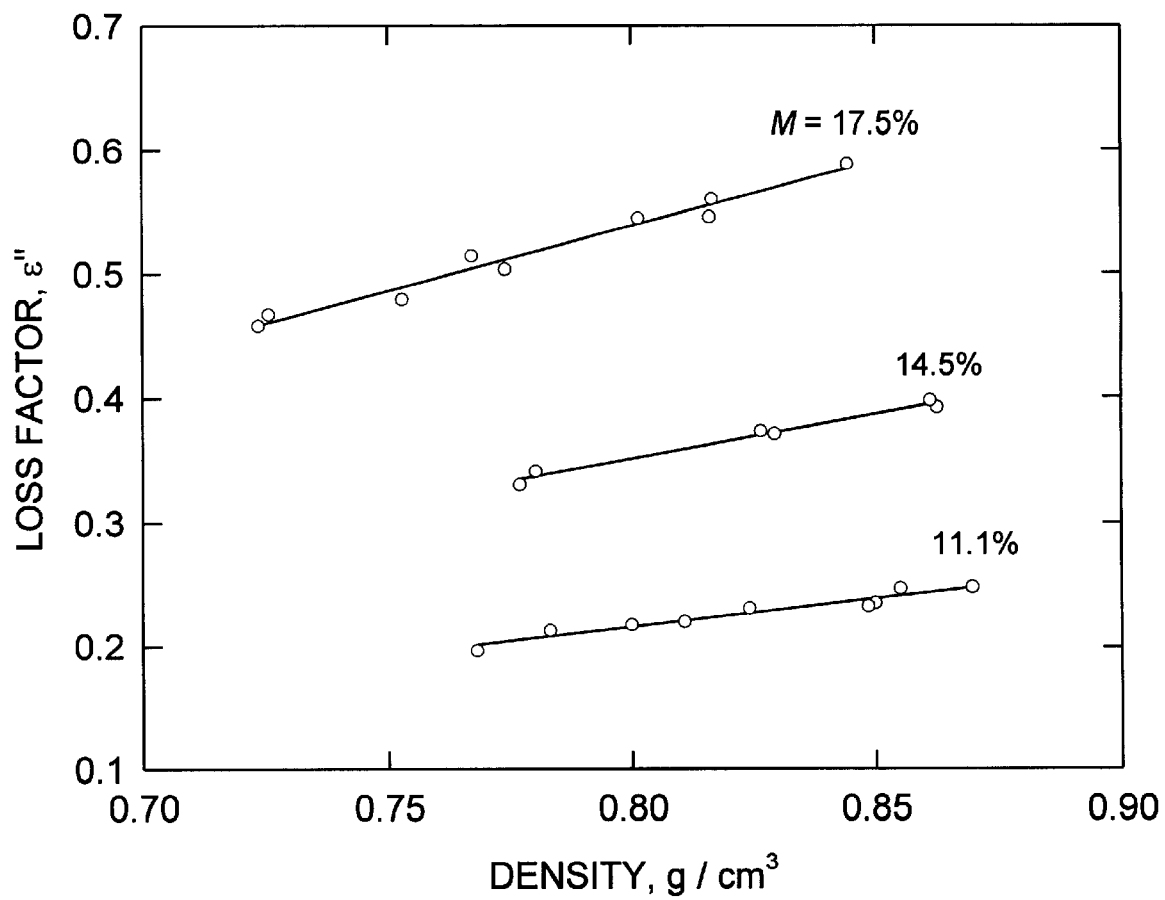
FIG 4b is a graph showing the density dependence of loss factor of hard red winter wheat at 14.2 GHz, 24° C. and indicated moisture contents.

Bulk density is usually defined as the ratio of the total mass to the total volume. FIGS. 4a and 4b show the variations of ε' and ε" with the bulk density for different moisture contents measured at 14.2 GHz and room temperature of approximately 24° C.+1 0C. Both ε' and ε" increase in a linear fashion with density. When analyzing these variations, one should keep in mind that the relative complex permittivity considered here is the average effective permittivity measured for a mixture consisting of air and wheat kernels. For a sample holder of fixed volume, by changing the density, the air and kernel proportions are changed, and so the amount of water interacting with the incident wave is also changed. However, at the kernel level, the dielectric properties are constant and assumed equal within the same sample of a given moisture content.

Figure 5A:
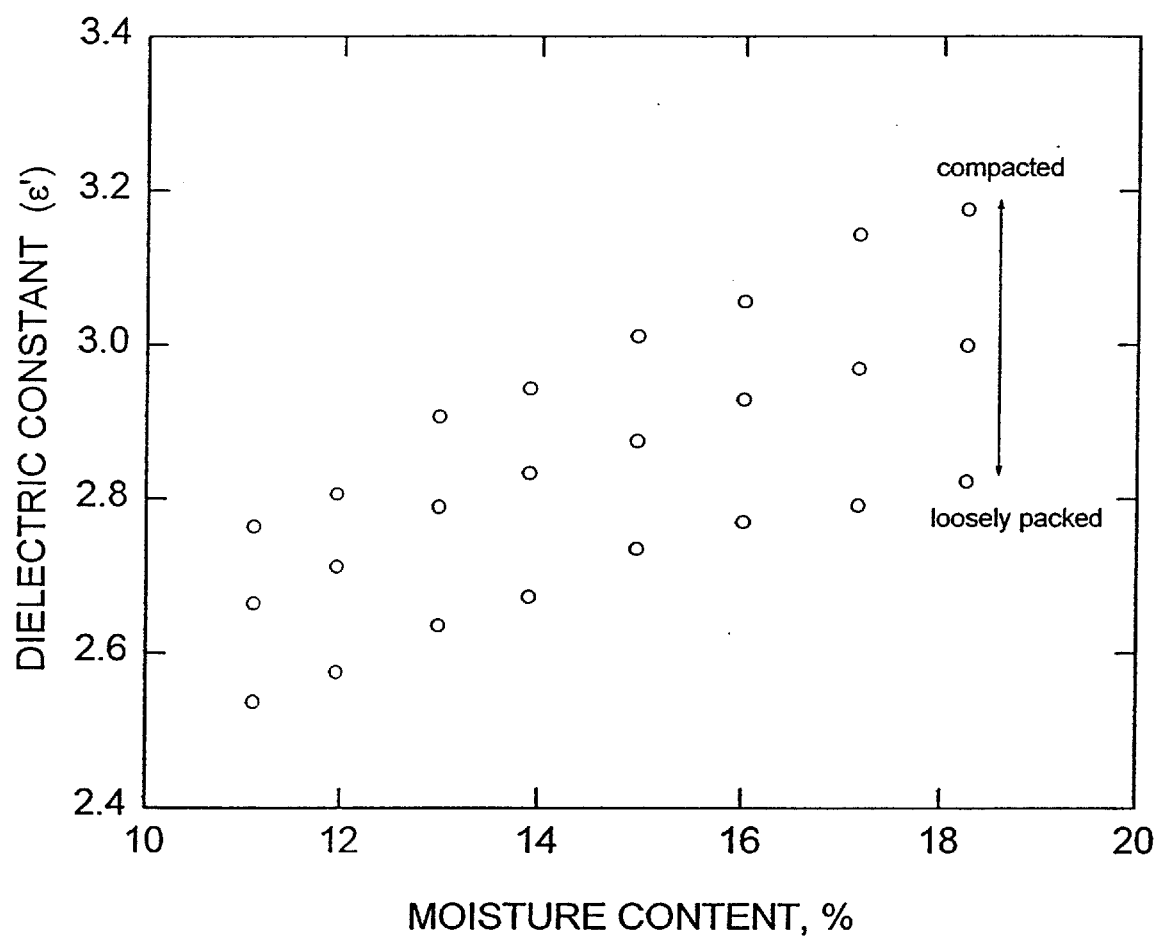
FIG. 5a is a graph showing moisture dependence of the dielectric constant of hard red winter wheat at 14.2 GHz, 24° C., and three different bulk densities ranging from loosely packed to compacted.
Figure 5B:
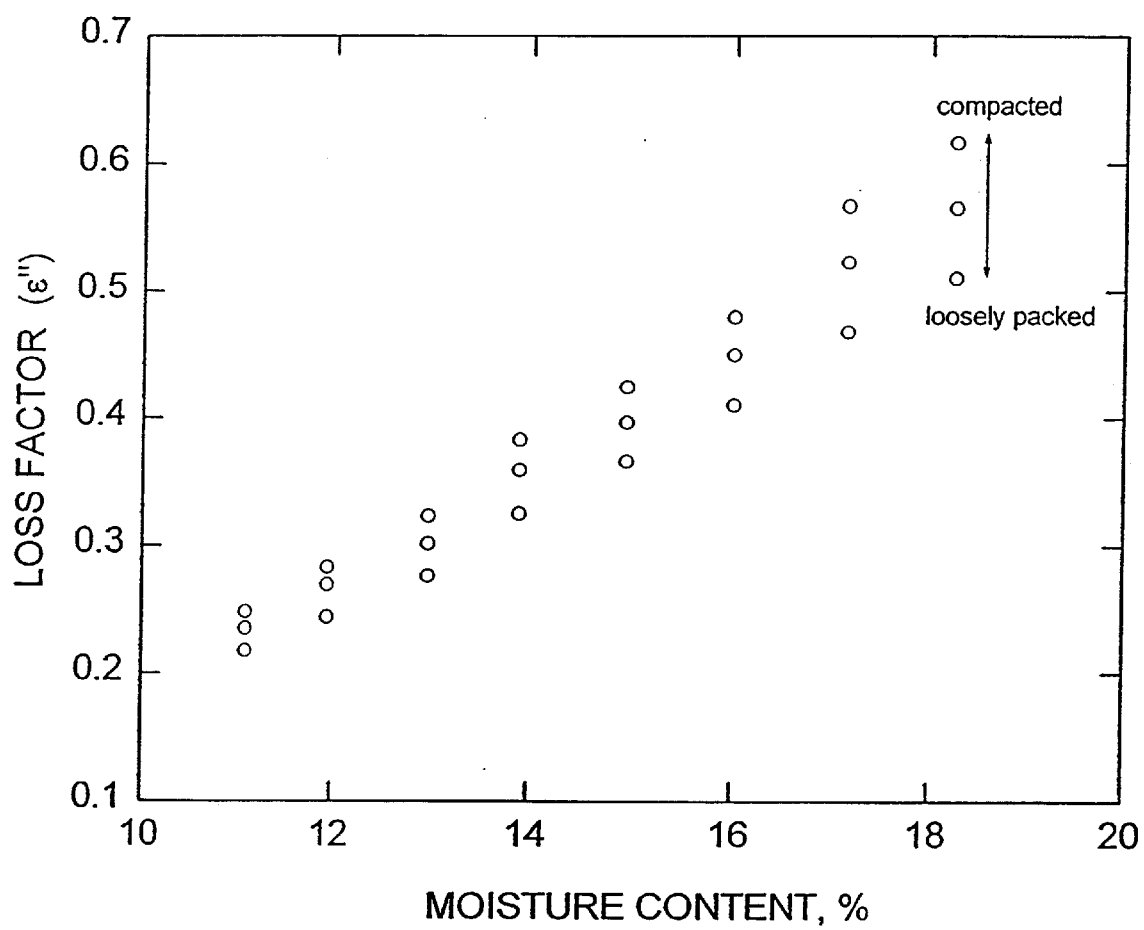
FIG. 5b is a graph showing moisture dependence of the loss factor of hard red winter wheat at 14.2 GHz, 24° C., and three different bulk densities ranging from loosely packed to compacted.

The variations of ε' and ε" with moisture content are shown in FIGS. 5a and 5b for three different densities ranging from loosely packed to compacted. Since the permittivity of water is large compared to that of dry material (typically the real part is about 3 and the imaginary part is expected to be very small [Hasted, Aqueous Dielectrics, Chapman and Hall, London, 237, 1973]), the measured dielectric constant and loss factor show significant variations with moisture content. A change of about 8% in moisture content produces, on average, a variation of about 12% for ε' and, as expected (Hasted, supra), a more important variation of about 140% for ε". Similar trends were found at other temperatures over the investigated frequency range.

FIGS. 4a, 4b, 5a and 5b show that density and moisture content affect the dielectric properties in a similar fashion. Therefore, when moisture content is the target parameter, the density fluctuations will cause undesirable errors in moisture determination. These errors can be reduced by a separate measurement of density which always involves an additional cost as discussed above.

Figure 6:
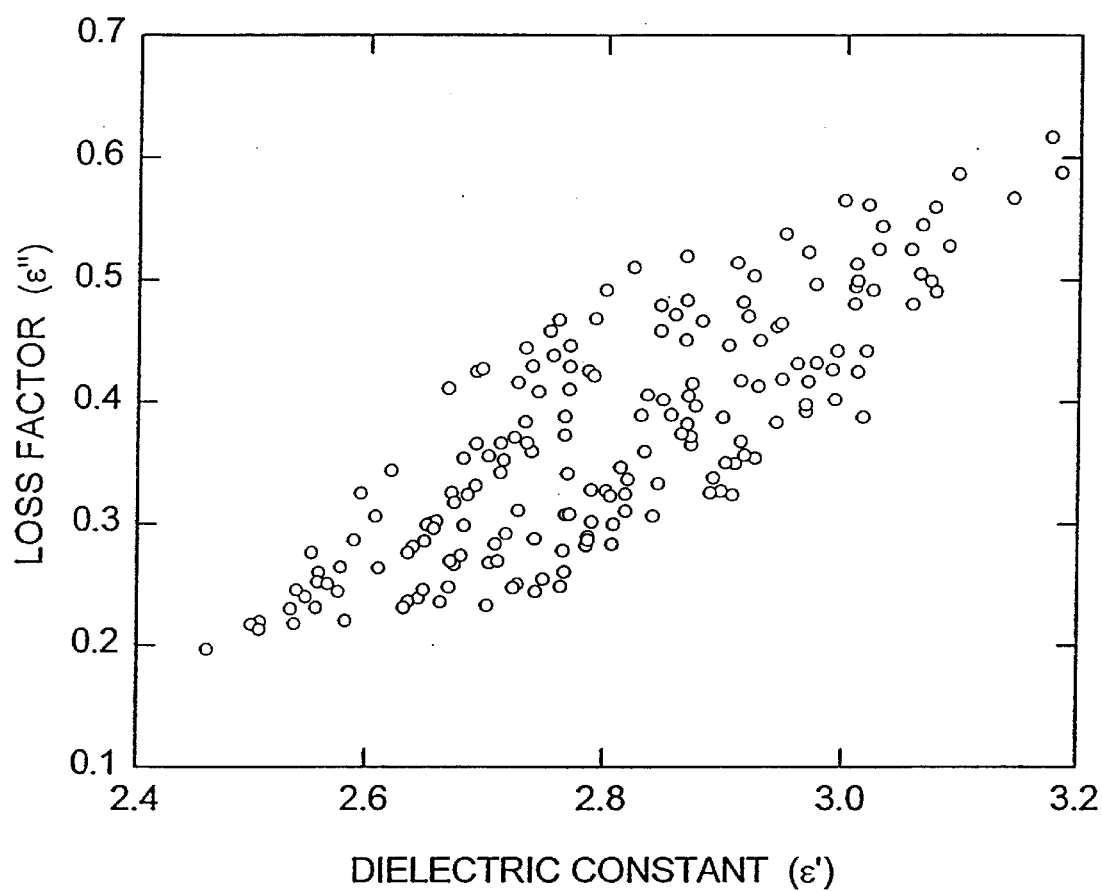
FIG. 6 is a graph showing the locus in the complex plane of the relative complex permittivities of samples of hard red winter wheat of different moisture contents and bulk densities at 14.2 GHz and 24° C.
Figure 7:
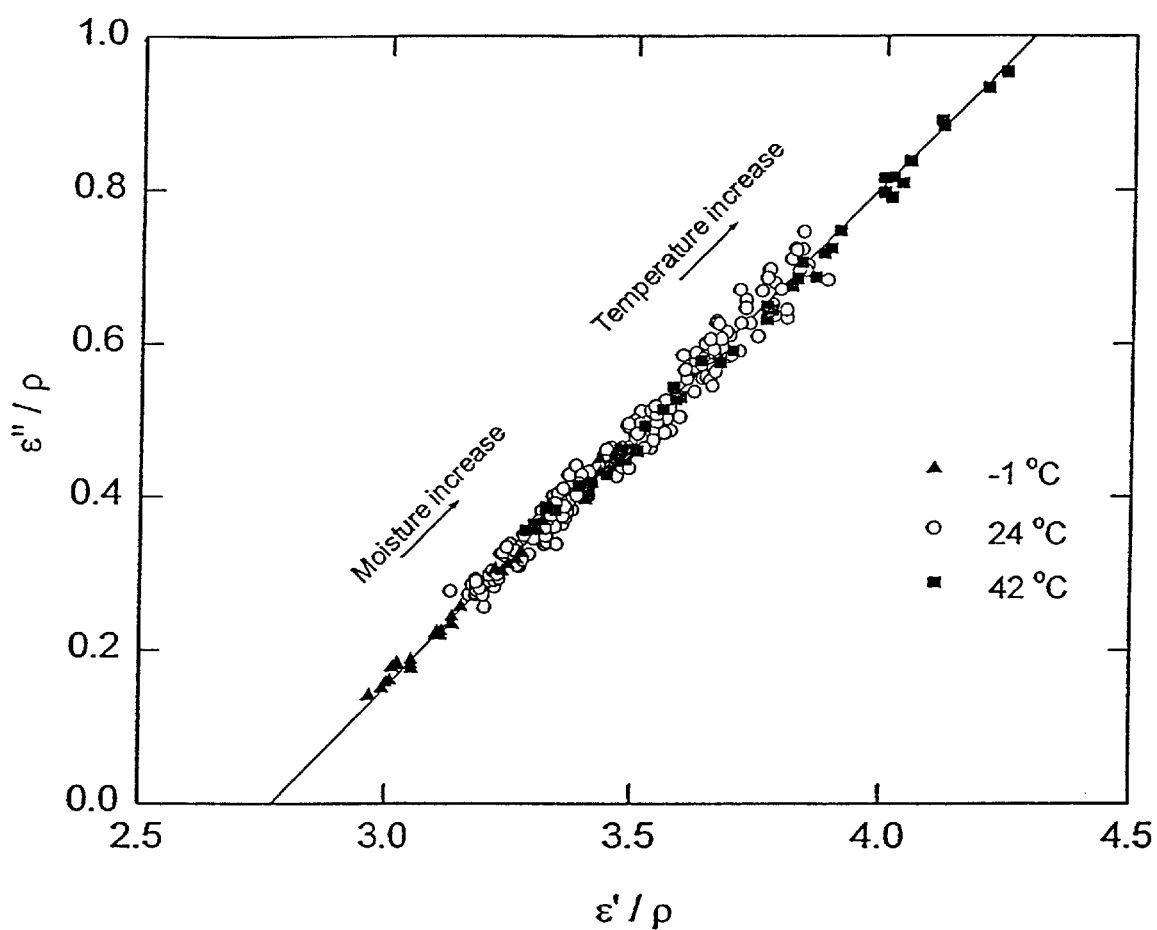
FIG. 7 is the locus in the complex plane of the relative permittivities divided by bulk density of samples of hard red winter wheat of different moisture contents at 14.2 GHz and indicated temperatures.

FIG. 6 shows the loss factor plotted against the dielectric constant at about 14.2 GHz and 24° C. for different moisture contents and bulk densities. A cluster of data points is obtained in the complex plane. The nature of the dependence of the two components of the relative complex permittivity on bulk density (FIGS. 4a and 4b) implies that dividing both ε' and ε" by the bulk density should reduce the density effect. This is shown in FIG. 7 where the points are now located along a line in the complex plane. Data obtained at the two extreme temperatures, approximately −1° C. and +42° C. are identified. These points lie on the same line and overlap those measured at about +24° C., with data corresponding to the lowest temperature located in the lower region of the graph. Therefore, at a given frequency, the temperature effect corresponds to a translation along the line. Similar dependence was observed at other frequencies. This reflects the thermal behavior of "bound" water in organic materials, where the water molecular dipoles occupy well defined sites and are not free to rotate because of their bonds with surrounding neighbors and the nature of forces acting on these dipoles. There are different degrees of binding and each water molecule may have up to three bonds (ice) depending on the structure and composition of the material and the amount of water available. As the temperature increases, the mobility of the water molecules increases, making their contribution to the polarization of the medium higher and increasing the losses at the same time. In contrast, the lower the temperature, the slower the action of the molecular dipoles, and the losses tend to be negligible. By extrapolation, the losses reach the zero value at a certain temperature where the electrical behavior of the material tends toward that of the dry material (FIG. 7).

Figure 8:
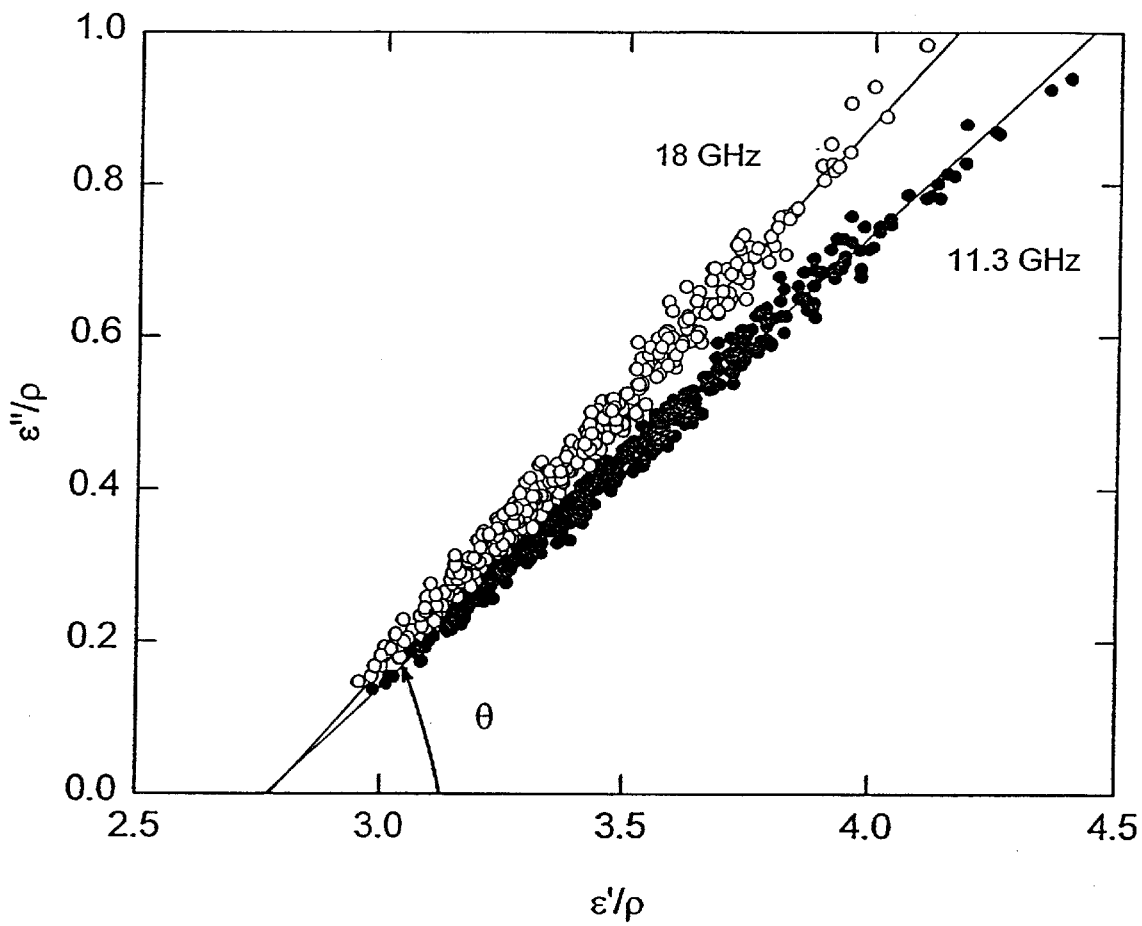
FIG. 8 is a graph showing the locus in the complex plane of the relative complex permittivities divided by bulk density of samples of hard red winter wheat of different moisture contents at two extreme frequencies and different temperatures $-1 \leq T(T) \leq +42$. Also shown is the angle of rotation in the complex plane, $$\theta = \arctan\left(\frac{\frac{\varepsilon''}{\rho}}{\frac{\varepsilon'}{\rho} - k}\right)$$

At each frequency, a data set is formed by data points, corresponding to measurements at all temperatures and moisture contents (396 data points), which can be fitted with a linear regression of the form $$\frac{\varepsilon''}{\rho} = a_f\left(\frac{\varepsilon'}{\rho} - k\right) a_f \text{ and } a_f k$$

where are the slope and the intercept, respectively. The values $a_f$, k, and the coefficients of determination for different frequencies are given in Table 1 below. In FIG. 8, $$\frac{\varepsilon''}{\rho} \text{ versus } \frac{\varepsilon'}{\rho}$$

is plotted for all temperatures and moisture contents for the lowest and highest frequency considered in this example. Similar lines are obtained at the other frequencies with a slope increasing as the frequency increases (Table 1). The intercept constant k is essentially constant for all frequencies and has an average value of about 2.76. All the lines cross the $$\frac{\varepsilon'}{\rho}$$

axis at a common point (2.76,0). This point corresponds to $$\frac{\varepsilon''}{\rho} = 0$$

and can be considered as the coordinates, in the complex plane, of the dielectric properties of the dry material. Measurements carried out on samples of oven dry material over the same frequency range and at room temperature provided a value of about 2.74 for $$\frac{\varepsilon'}{\rho},$$

which is in good agreement with that obtained by graphical extrapolation. The dielectric properties of the dry material are nondispersive and thus showed no variations with frequency. Although the microwave measurements on the oven dry material were made at room temperature, there is no reason to expect these properties to be temperature dependent. The frequency effect can be described as a rotation of angle θ in the complex plane, $$\theta = \arctan\left(\frac{\frac{\varepsilon''}{\rho}}{\frac{\varepsilon'}{\rho} - k}\right) \tag{9}$$

with θ independent of moisture content and temperature and a function of the frequency alone. Therefore, a relationship between the slope $a_f$ and the frequency $f$ as follows $$a_f = 0.0184 f + 0.3826 \, r^2 = 0.993 \tag{10}$$

where $f$ is the frequency in GHz.

As a result from equation 5, the bulk density can be expressed in terms of ε' and ε" by equation 6. Examination of the dimensions in equation 6 shows that a simple relationship exists at any given frequency between the bulk density and the two components of the relative complex permittivity. Therefore, from the measured dielectric constant and loss factor and knowledge of $a_f$ and the intercept k, and the relation in equation 10, the bulk density can be determined at any frequency, moisture content, and temperature. FIG. 9 shows the predicted bulk density using equation 6 against measured bulk density for hard red winter wheat for data obtained at 11.3 GHz. The standard error of calibration (SEC) is 0.009 g/cm³ (Table 4 below).

The loss tangent is the entity that best describes the energy balance and losses in dielectrics. It is proportional to the ratio of the energy dissipated to that stored in the medium. At high frequencies, when an electromagnetic wave interacts with a moist substance, water is the dominant factor associated with the energy dissipated in the material. Therefore, a density-independent function based on the loss tangent should better describe the wave-material interaction from the energy point of view. FIG. 10 shows the variations of tan δ with moisture content. As with ε' and ε", tan δ increases with moisture content. However, the density effect is still visible at each moisture level. In order to reduce this effect, a density-independent function ψ is defined as the ratio of tan δ to the bulk density given in equation 6. In equation 7, ψ is fully defined in terms of dielectric properties of the material, the intercept constant k which corresponds to the dielectric properties of the dry material, and a frequency factor of $a_f$ independent of moisture content and temperature. For practical purposes, the fewer extrinsic parameters involved in the calibration equation, the easier is the calibration procedure. Examination of equation 7 indicates that at a given frequency, the product $ka_f$ is a constant and thus can be omitted. Therefore, the density independent function ψ when used for calibration in a measuring system operating at a single frequency can be simplified to ζ as shown in equation 8. In this simplified form in equation 8, only one extrinsic parameter is needed, namely the frequency factor $a_f$. FIG. 11 shows the variations of ζ with moisture content, for the same data as in FIG. 10. The function ζ increases in quadratic fashion with the moisture content. The spread of points at each moisture level is significantly reduced if not completely removed. In FIG. 12, ζ is plotted versus density for the same data used in FIG. 4a and 4b; the straight lines are now essentially parallel to the ρ axis. Both FIGS. 11 and 12 confirm the density independent character of ζ.

To complete the study of ζ, the frequency and temperature dependence have to be considered. The frequency dependence is shown in FIG. 13 for two levels of moisture. ζ decreases slightly with increasing frequency, similar to the variation with frequency noted for ε' and ε". Therefore, for a moisture sensing instrument operating at a single frequency, the frequency selection should be based on other criteria, such as dynamic range and sensitivity of the system, the thickness of the layer, the dimensions and shape of the kernels (scattering phenomenon), etc.

The temperature dependence is illustrated in FIG. 14 for two levels of moisture. The density-independent function ζ is a linear function of temperature with a positive slope $$\left(\frac{d\varepsilon}{dT} > 0\right)$$

which is greater for higher moisture contents. This reflects the thermal behavior of "bound" water.

Because of the quadratic nature of the variations of ζ with moisture content (FIG. 11), the square root of ζ is considered rather than ζ to establish a calibration equation for moisture content determination at a given frequency and temperature. In FIG. 15, √ζ at 14.2 GHz is plotted versus moisture content at different temperatures. A network of essentially parallel lines is obtained with temperature as a parameter. As expected, the square root of ζ increases almost linearly with increasing moisture content at any temperature. At 24° C., a change of about 8% in moisture content, produces a variation of about 50% for √ζ which is between that of the dielectric constant and loss factor (See moisture dependence supra). At each temperature, a linear regression of the form $$\sqrt{\zeta} = a \times M + B \tag{11}$$

was used to fit the data, where a is the slope, M is the moisture content in percent, and B is the intercept. The values of a, B, and the coefficient of determination r² are given in Table 2, below, at different frequencies and temperatures. The high values of r² show the high correlation between √ζ and M and demonstrate that the density-independent calibration function ζ can be of potential use for moisture content prediction. The slope a generally shows very small temperature dependence, and considering the errors in ε' and ε", a can be assumed constant. In contrast, B increases with temperature. An explicit relation can be established empirically between B and the temperature.

For example, at 14.2 GHz and 9≦T (° C.)≦34, a linear regression gives $$B(T) = 9.77 \times 10^{-4} T + 0.0206 \; r^2 = 0.9902 \tag{12}$$

where T is the temperature in degree Celsius.

Therefore, when equation 11 is used, the moisture content in percent, at a given frequency and temperature, can be calculated from the following calibration equation:

$$M\% = \frac{\sqrt{\xi(a_f, \varepsilon', \varepsilon'') - B(T)}}{a} \tag{13}$$

In FIG. 16, the moisture predicted by equation 13 at room temperature and about 14.2 GHz is plotted versus oven moisture content determinations. The standard error of calibration (SEC) was 0.25% moisture content. The standard error of calibration is defined as $$SEC = \sqrt{\frac{1}{n-p-1} \times \sum_{i=1}^{m} (\Delta M_i)^2} \tag{14}$$

where n is the number of samples, p the number of variables in the regression equation with which the calibration is performed and $\Delta M_i$ is the difference in moisture content predicted and that determined by the reference method for the ith sample. The standard error of calibration, as defined by equation 14, is a good indicator often used to evaluate the calibration procedure. Values of the SEC in percent moisture content are illustrated for 7 different frequencies at 24° C. in Table 3 below. These values are, on average, of the same order as the error for oven drying techniques, although a slight increase with frequency is observed. This is mainly due to errors in attenuation measurements at higher frequencies and the limited dynamic range of the vector network analyzer. However, measurements at only a single frequency are required for the method of the present invention.

The accuracy with which M is determined, depends on the validity of equation 11 and is mainly related to the accuracy with which the dielectric properties of the material are measured. In this respect, the choice of the measurement technique is important. Moreover, as in any calibration procedure for indirect determination of a particular parameter, moisture content in this instance, the reliability is dependent on the accuracy of the reference method.

Both bulk density and moisture content of particulate materials can be determined directly from measured microwave dielectric properties. An explicit relation between the bulk density and the two components of the relative permittivity is given and a new density-independent calibration function for moisture content prediction is defined. Explicit calibration equations for bulk density and moisture content determination can be generated at different frequencies and temperatures from Tables 1 and 2. The new density-independent function better describes the wave-material interaction from the energy point of view and integrates both frequency and temperature effects. Its' frequency, temperature, and moisture content dependence are similar to those of the relative complex permittivity. One of the attractive features of this function is its independence from the measurement techniques used to determine material permittivity and, thus, it provides more freedom of choice for the appropriate technique for moisture sensing.

TABLE 1

| Freq., GHz | 11.3 | 12.3 | 13.3 | 14.2 | 15.2 | 16.8 | 18 |
|---|---|---|---|---|---|---|---|
| $a_f$ | 0.5960 | 0.6060 | 0.6255 | 0.6474 | 0.6596 | 0.6902 | 0.7187 |
| k | 2.765 | 2.776 | 2.776 | 2.758 | 2.747 | 2.756 | 2.773 |
| $r^2$ | 0.9997 | 0.9875 | 0.9888 | 0.9900 | 0.9884 | 0.9891 | 0.9868 |

TABLE 2

| Temp. °C. | -1 | 9 | 16 | 24 | 34 | 42 |
|---|---|---|---|---|---|---|
| F = 11.3 GHz | | | | | | |
| a | 0.0173 | 0.0176 | 0.0186 | 0.0187 | 0.0191 | 0.0174 |
| B | -0.0023 | 0.02 | 0.0242 | 0.0392 | 0.0546 | 0.0933 |
| $r^2$ | 0.9858 | 0.9916 | 0.9911 | 0.9883 | 0.9946 | 0.9924 |
| F = 14.2 GHz | | | | | | |
| a | 0.0161 | 0.0160 | 0.0172 | 0.0174 | 0.0183 | 0.0177 |
| B | 0.0076 | 0.0303 | 0.0348 | 0.0446 | 0.0540 | 0.08 |
| $r^2$ | 0.9811 | 0.9905 | 0.9878 | 0.9855 | 0.9913 | 0.9921 |
| F = 18 GHz | | | | | | |
| a | 0.0144 | 0.0148 | 0.016 | 0.017 | 0.0179 | 0.0182 |
| B | 0.0187 | 0.0362 | 0.0376 | 0.043 | 0.0488 | 0.0636 |
| $r^2$ | 0.9843 | 0.9888 | 0.9845 | 0.9772 | 0.9852 | 0.9857 |

TABLE 3

STANDARD ERROR OF CALIBRATION (SEC)
AT DIFFERENT FREQUENCIES AND 24 °C.

| fGHz | 11.3 | 12.3 | 13.3 | 14.2 | 15.2 | 16.8 | 18 |
|---|---|---|---|---|---|---|---|
| SEC % | 0.225 | 0.212 | 0.223 | 0.252 | 0.246 | 0.284 | 0.317 |

TABLE 4

STANDARD ERROR OF CALIBRATION (SEC) FOR
BULK DENSITY DETERMINATION AT DIFFERENT FREQUENCIES

| f, GHz | 11.3 | 12.3 | 13.3 | 14.2 | 15.2 | 16.8 | 18 |
|---|---|---|---|---|---|---|---|
| SEC g/cm$^3$ | 0.00905 | 0.01076 | 0.010149 | 0.00911 | 0.00982 | 0.00891 | 0.00898 |

The foregoing detailed description is for the purposes of illustration. Others skilled in the art can apply the knowledge described to other hygroscopic and/or particulate materials. Such detail is solely for that purpose and those skilled in the art can make variations therein without departing from the spirit and scope of the invention.

INDEX OF THE ELEMENTS

10. Measuring System
11. Radio-frequency Source
12. Sensing Elements
13. Transmitting Antenna
14. Receiving Antenna
15. Material
18. Coaxial Cables
20. Ports
21. Measuring Unit
22. Vector Network Analyzer
24. Sample Holder
26. Computer
28. Printer

We claim:

1. A method for determining moisture content of a material comprising
   (a) locating a material in a radio-frequency measuring device comprising a source, sensing elements and a radio-frequencies properties measuring unit,
   (b) measuring the radio-frequency properties of said material,
   (c) calculating the dielectric constant $\epsilon'$ and the loss factor $\epsilon''$, and
   (d) determining percent moisture content, M%, of said material using $\epsilon'$ and $\epsilon''$ obtained in step (c) using a calibration equation as follows:

$$M\% = \frac{\sqrt{\xi(a_f, \varepsilon', \varepsilon'')} - B(T)}{a}$$

wherein $a_f$, B and a are constants specific to said material, and $\zeta$ is a density-independent function determined by the following equation:

$$\xi = \frac{1}{a_f \varepsilon' - \varepsilon''}\left(\frac{\varepsilon''}{\varepsilon'}\right).$$

2. The method of claim 1 wherein said material is a hygroscopic particulate material.

3. A method for determining bulk density of a material comprising
   (a) locating a material in a radiofrequency measuring device comprising a source, sensing elements and a radio-frequency properties measuring unit,
   (b) measuring the radio-frequency properties of said material,
   (c) calculating the dielectric constant $\epsilon'$ and the loss factor $\epsilon''$, and
   (d) determining bulk density, ρ, of said material using $\epsilon'$ and $\epsilon''$ obtained in step (c) using the following equation:

$$\rho = \frac{1}{k}\left(\frac{a_f \varepsilon' - \varepsilon''}{a_f}\right)$$

wherein k, in $g^{-1} \cdot cm^3$ and $a_f$ are constants specific to said material.

4. The method of claim 3 wherein said material is a hygroscopic and/or particulate material.

5. A method for determining moisture content and bulk density of a material comprising
   (a) locating a material in a radio-frequency measuring device comprising a source, sensing elements, and a radio-frequency properties measuring unit,
   (b) measuring the radio-frequency properties of said material,
   (c) calculating the dielectric constant $\epsilon'$ and the loss factor $\epsilon''$,
   (d) determining percent moisture content, M%, of said material using $\epsilon'$ and $\epsilon''$ obtained in step (c) using a calibration equation as follows:

$$M\% = \frac{\sqrt{\xi(a_f, \varepsilon', \varepsilon'')} - B(T)}{a}$$

wherein $a_f$, B and a are constants specific to said material, and $\zeta$ is a density-independent function determined as follows:

$$\xi = \frac{1}{a_f \varepsilon' - \varepsilon''} \left( \frac{\varepsilon''}{\varepsilon'} \right), \text{ and}$$

(e) determining bulk density, $\rho$, of said material using $\epsilon'$ and $\epsilon''$ obtained in step (c) using the following:

$$\rho = \frac{1}{k} \left( \frac{a_f \varepsilon' - \varepsilon''}{a_f} \right)$$

wherein k, in $g^{-1} \cdot cm^3$, and $a_f$ are all constants specific to said materials; and percent moisture content and bulk density are simultaneously and independently measured.

6. The method of claim 1 wherein said measured radio-frequency property is selected from the group consisting of complex impedance, complex reflection coefficient, complex transmission coefficient, and resonant frequency and quality factor.

7. The method of claim 6 wherein the radio-frequency property measured is complex transmission coefficient.

8. The method of claim 1 wherein said radio-frequency measuring device is a free-space transmission microwave system, said sensing elements are a transmitting antenna and a receiving antenna, and said radio-frequency measuring unit is a vector network analyzer.

9. The method of claim 3 wherein said measured radio-frequency property is selected from the group consisting of complex impedance, complex reflection coefficient, complex transmission coefficient, and resonant frequency and quality factor.

10. The method of claim 9 wherein the radio-frequency property measured is complex transmission coefficient.

11. The method of claim 3 wherein said radio-frequency measuring device is a free-space transmission microwave system, said sensing elements are a transmitting antenna and a receiving antenna, and said radio-frequency measuring unit is a vector network analyzer.

12. The method of claim 5 wherein said measured radio-frequency property is selected from the group consisting of complex impedance, complex reflection coefficient, complex transmission coefficient, and resonant frequency and quality factor.

13. The method of claim 12 wherein the radio-frequency property measured is complex transmission coefficient.

14. The method of claim 5 wherein said radio-frequency measuring device is a free-space transmission microwave system, said sensing elements are a transmitting antenna and a receiving antenna, and said radio-frequency measuring unit is a vector network analyzer.

15. A method for determining percent moisture content of a material comprising (a) locating a material in a free-space transmission microwave system comprising a synthesized sweeper, a transmitting antenna, a receiving antenna and a vector network analyzer, (b) measuring complex transmission coefficient, (c) calculating dielectric constant $\epsilon'$ and $\epsilon''$, and (d) determining percent moisture content, M%, of said material using $\epsilon'$ and $\epsilon''$ obtained in step (c) using a calibration equation:

$$M\% = \frac{\sqrt{\xi(a_f, \varepsilon', \varepsilon'')} - B(T)}{a}$$

$a_f$, B and a are constants specific to said material, and $\zeta$ is a density-independent function determined as follows:

$$\xi = \frac{1}{a_f \varepsilon' - \varepsilon''} \left( \frac{\varepsilon''}{\varepsilon'} \right).$$

16. The method of claim 15 further comprising determining bulk density, $\rho$, of said material using $\epsilon'$ and $\epsilon''$ obtained in step (c) using the following:

$$\rho = \frac{1}{k} \left( \frac{a_g \varepsilon' - \varepsilon''}{a_f} \right)$$

wherein k, in $g^{-1} \cdot cm^3$, and $a_f$ are all constants specific to said materials; and percent moisture content and bulk density are simultaneously and independently measured.

17. The method of claim 15 wherein said material is a hygroscopic particulate material.

* * * * *

UNITED STATES PATENT AND TRADEMARK OFFICE
CERTIFICATE OF CORRECTION

PATENT NO. : 6,147,503
DATED : November 14, 2000
INVENTOR(S) : Samir Trabelsi, Andrzej W. Kraszewski and Stuart O. Nelson It is certified that error appears in the above-identified patent and that said Letters Patent is hereby corrected as shown below:

<u>Title page,</u>
Item [19], should read as follows: Trabelsi et al.

Item [75], should read as follows:
Inventors: Samir Trablesi, Andrzej W. Kraszewski and Stuart O. Nelson Signed and Sealed this Ninth Day of October, 2001

*Attest:*

*Nicholas P. Godici*

NICHOLAS P. GODICI
*Attesting Officer*    *Acting Director of the United States Patent and Trademark Office*

UNITED STATES PATENT AND TRADEMARK OFFICE
CERTIFICATE OF CORRECTION

PATENT NO. : 6,147,503  
DATED : November 14, 2000  
INVENTOR(S) : Samir Trabelsi, Andrzej W. Kraszewski and Stuart O. Nelson Page 1 of 1

It is certified that error appears in the above-identified patent and that said Letters Patent is hereby corrected as shown below:

<u>Title page,</u>  
First named Inventor: Trabelsi et al.

Inventors: Samir Trabelsi, Andrzej W. Kraszewski and Stuart O. Nelson

This Certificate of Correction supercedes certificate issued on October 9, 2001.

Signed and Sealed this

Second Day of April, 2002

*Attest:*

JAMES E. ROGAN  
*Attesting Officer*     *Director of the United States Patent and Trademark Office*